(12) United States Patent
Huber et al.

(10) Patent No.: US 8,810,901 B2
(45) Date of Patent: Aug. 19, 2014

(54) WAVELENGTH-TUNABLE LIGHT SOURCE

(75) Inventors: Robert Alexander Huber, Schnaitsee (DE); Christoph Eigenwillig, Buchloe (DE); Benjamin Biedermann, München (DE)

(73) Assignee: Lightlab Imaging, Inc., Westford, MA (US)

( * ) Notice: Subject to any disclaimer, the term of this patent is extended or adjusted under 35 U.S.C. 154(b) by 413 days.

(21) Appl. No.: 13/061,090

(22) PCT Filed: Sep. 3, 2009

(86) PCT No.: PCT/EP2009/061419
§ 371 (c)(1),
(2), (4) Date: Feb. 25, 2011

(87) PCT Pub. No.: WO2010/026197
PCT Pub. Date: Mar. 11, 2010

(65) Prior Publication Data
US 2011/0157686 A1    Jun. 30, 2011

(30) Foreign Application Priority Data
Sep. 3, 2008 (DE) .......................... 10 2008 045 634

(51) Int. Cl.
*H01S 4/00* (2006.01)
*H01S 3/098* (2006.01)
*H01S 3/10* (2006.01)
*H01S 5/00* (2006.01)

(52) U.S. Cl.
USPC ............................ 359/337.2; 372/18; 372/20

(58) Field of Classification Search
USPC ............................ 359/337.2, 344; 372/18, 20
See application file for complete search history.

(56) References Cited

U.S. PATENT DOCUMENTS 5,263,037 A    11/1993   Trutna, Jr. et al.
5,321,501 A     6/1994   Swanson et al.
(Continued)

FOREIGN PATENT DOCUMENTS

| EP | 0 524 382 | 1/1993 |
| WO | 03/096106 | 11/2003 |
| WO | 2010/026197 | 3/2010 |

OTHER PUBLICATIONS

Chang T. et al., Pulsed Dye-Laser with Grating and Etalon in a Symmetric Arrangement. Appl. Opt. 1980; 19 (21): 3651-3645.

(Continued)

*Primary Examiner* — Eric Bolda
(74) *Attorney, Agent, or Firm* — Marshall, Gerstein & Borun LLP

(57) ABSTRACT

In at least one embodiment of the wavelength-tunable light source (1), it comprises an output source (2), which is capable in operation of generating electromagnetic radiation (R). Furthermore, the light source (1) has a wavelength-selective first filter element (5), which is situated downstream from the output source (2). Moreover, the light source (1) contains a first amplifier medium (3), which is situated downstream from the first filter element (5) and is capable of at least partial amplification of the radiation (R) emitted by the output source (2). The light source (1) further comprises at least one wavelength-selective second filter element (6), which is situated downstream from the first amplifier medium (3), the second filter element (6) having an optical spacing (L) to the first filter element (5). The first filter element (5) and the at least one second filter element (6) are tunable via a control unit (11), which the light source (1) has. The filter elements (5, 6) are tuned for this purpose so that first filter element (5) and second filter element (6) are transparent to a partial radiation (P) of the radiation (R) in a time delay (T) to one another, the delay (T) being equal to the quotient of the optical spacing (L) and the speed of light in vacuum (c).

10 Claims, 20 Drawing Sheets

(56) References Cited

U.S. PATENT DOCUMENTS

Figure 3:
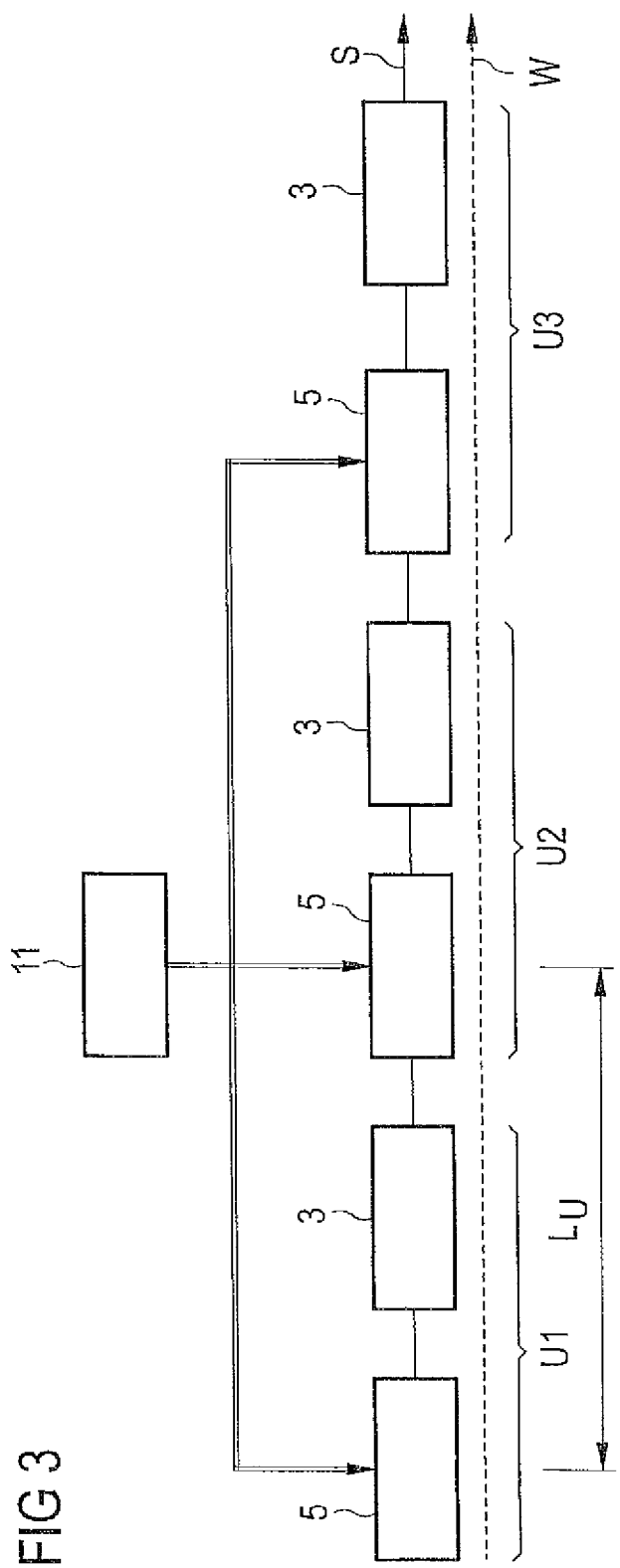

| | | | |
|---|---|---|---|
| 5,459,570 A | 10/1995 | Swanson et al. | |
| 5,465,147 A | 11/1995 | Swanson | |
| 5,500,762 A | 3/1996 | Uchiyama et al. | |
| 5,509,093 A | 4/1996 | Miller et al. | |
| 5,574,739 A | 11/1996 | Carruthers et al. | |
| 5,619,368 A | 4/1997 | Swanson | |
| 5,701,195 A * | 12/1997 | Chikama | 359/341.43 |
| 5,748,598 A | 5/1998 | Swanson et al. | |
| 5,784,352 A | 7/1998 | Swanson et al. | |
| 5,822,476 A * | 10/1998 | Jopson | 385/27 |
| 5,956,355 A | 9/1999 | Swanson et al. | |
| 5,991,477 A | 11/1999 | Ishikawa et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,282,215 B1 | 8/2001 | Zorabedian et al. | |
| 6,373,632 B1 | 4/2002 | Flanders | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,608,711 B2 | 8/2003 | Flanders et al. | |
| 6,706,004 B2 | 3/2004 | Tearney et al. | |
| 6,816,515 B1 | 11/2004 | Yun et al. | |
| 6,879,851 B2 | 4/2005 | McNamara et al. | |
| 6,891,984 B2 | 5/2005 | Petersen et al. | |
| 7,061,618 B2 | 6/2006 | Atia et al. | |
| 7,075,058 B2 | 7/2006 | Chinn et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,414,779 B2 | 8/2008 | Huber et al. | |
| 7,415,049 B2 | 8/2008 | Flanders et al. | |
| 7,625,366 B2 | 12/2009 | Atlas | |
| 7,813,609 B2 | 10/2010 | Petersen et al. | |
| 7,848,791 B2 | 12/2010 | Schmitt et al. | |
| 7,884,945 B2 | 2/2011 | Srinivasan et al. | |
| 7,916,387 B2 | 3/2011 | Schmitt et al. | |
| 7,935,060 B2 | 5/2011 | Schmitt et al. | |
| 8,358,461 B2 * | 1/2013 | Huber et al. | 359/337.2 |
| 2002/0054614 A1 | 5/2002 | Jin | |
| 2002/0161351 A1 | 10/2002 | Samson et al. | |
| 2003/0179790 A1 | 9/2003 | Bouda et al. | |
| 2005/0078716 A1 | 4/2005 | Liu | |
| 2005/0201662 A1 | 9/2005 | Petersen et al. | |
| 2005/0265402 A1 | 12/2005 | Tanaka et al. | |
| 2006/0095065 A1 | 5/2006 | Tanimura et al. | |
| 2006/0109872 A1 | 5/2006 | Sanders | |
| 2008/0165366 A1 | 7/2008 | Schmitt | |
| 2009/0174931 A1 | 7/2009 | Huber et al. | |
| 2009/0306520 A1 | 12/2009 | Schmitt et al. | |
| 2010/0076320 A1 | 3/2010 | Petersen et al. | |
| 2010/0094127 A1 | 4/2010 | Xu | |
| 2010/0103964 A1 | 4/2010 | Huber | |
| 2010/0253949 A1 | 10/2010 | Adler et al. | |
| 2011/0007315 A1 | 1/2011 | Petersen et al. | |
| 2011/0051143 A1 | 3/2011 | Flanders et al. | |
| 2011/0051148 A1 | 3/2011 | Flanders et al. | |
| 2011/0071404 A1 | 3/2011 | Schmitt et al. | |
| 2011/0071405 A1 | 3/2011 | Judell et al. | |
| 2011/0101207 A1 | 5/2011 | Schmitt | |
| 2011/0151980 A1 | 6/2011 | Petroff | |

OTHER PUBLICATIONS

Klauminzer, GK, "Etalon-Grating Synchronized Scanning of a Narrowband Pulsed Dye Laser," Optical Engineering 1974; 13 (6): p. 528-530.

Takada, K. et al., "Rapidly-tunable narrowband light source with symmetrical crossing configuration for low coherence reflectometry," Electronics Letter, Jan. 5, 1995, vol. 31 (1) p. 63-65.

Takesue, et al., "Broad-Band Lightwave Synthesized Frequency Sweeper Using Synchronous Filtering," J. of Lightwave Technology, 22(3): 755-762 (2004).

Yun, S.H., et al., "Wavelength-Swept Fiber Laser with Frequency Shifted Feedback and Resonantly Swept Intra-Cavity Acoustooptic Tunable Filter," IEEE Journal of Selected Topics in Quantum Electronics, 3(4): 1087-1096 (1997).

Yun, S.H., et al., "High-speed wavelength-swept semiconductor laser with a polygon-scanner-based wavelength filter," Optics Letters, 28(20): 1981-1983 (2003).

Yun, S.H., et al., "Interrogation of fiber grating sensor arrays with a wavelength-swept fiber laser," Optics Letters, 23 (11): 843-845 (1998).

Huber, R., et al., "Fourier Domain Mode Locked Lasers for OCT imaging at up to 290 kHz sweep rates," Proc. of SPIE-OSA Biomedical Optics, SPIE vol. 5861: (2005).

Shimizu, K., et al., "Measurement of Rayleigh Backscattering in Single-Mode Fibers Based on Coherent OFDR Employing a DFB Laser Diode," IEEE Photonics Technology Letters, 3(11): 1039-1041 (1991).

Telle, et al., "Very rapid tuning of cw dye laser," Applied Physics Letters, 26(10): 572-574 (1975).

Written Opinion of the International Searching Authority mailed Jul. 15, 2010 (8 pgs.)

Aljada et al., "Experimental demonstration of a tunable laser using an SOA and an Opto-VLSI Processor," Optic Express, 15(15):9666-9671, Jul. 23, 2007.

Eigenwillig et al., "Wavelength Swept ASE Source," Proceedings of the SPIE—The International Society for Optical Engineering SPIE—The International Society for Optical Engineering USA, vol. 7372, 2009, 4 pgs.

Takada, et al., "Loss distribution measurement of silica-based waveguides by using a jaggedness-free optical low coherence reflectometer," Electronics Letters, 30(17):1441-1443, Aug. 18, 1994.

Takada, et al., "Tunable Narrow-Band Light Source Using Two Optical Circulators," IEEE Photonics Technology Letters, 9(1):91-93, Jan. 1997.

* cited by examiner

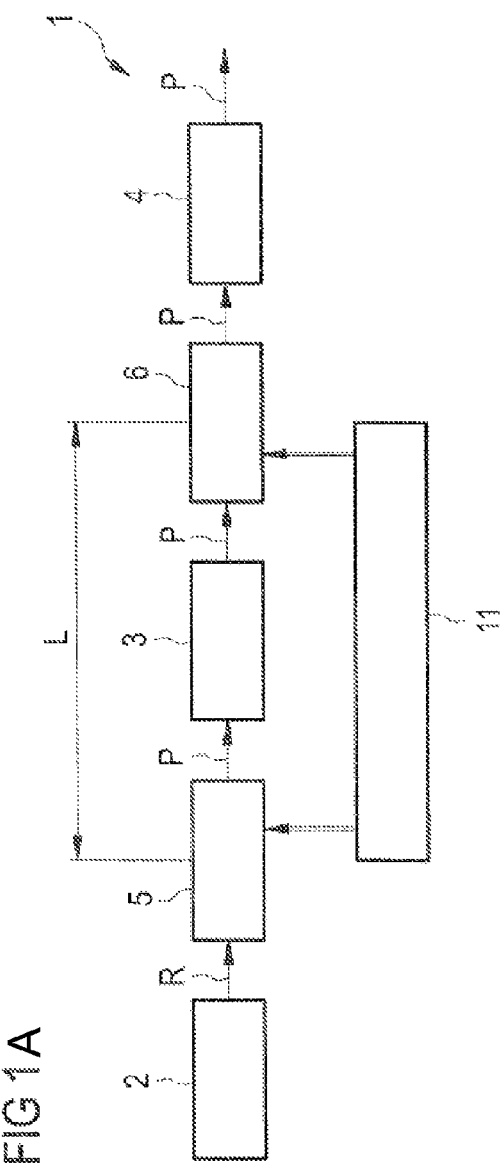
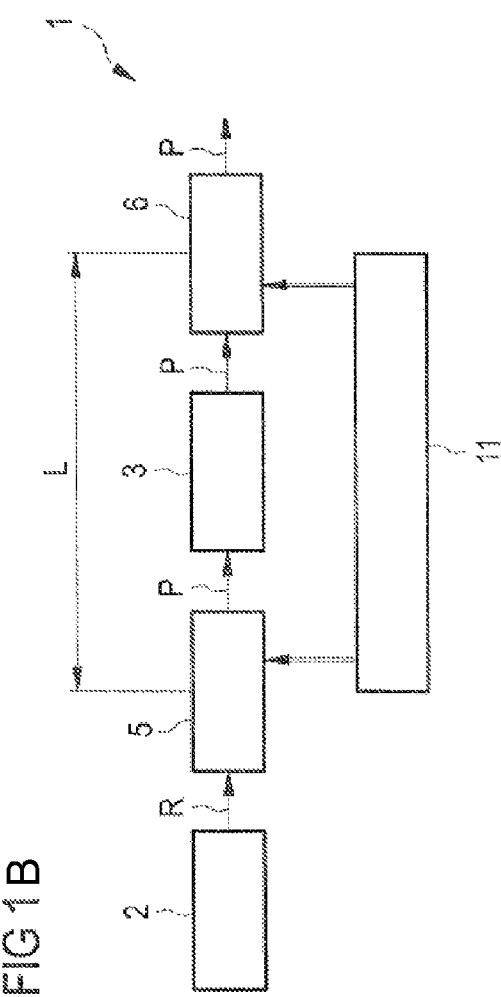

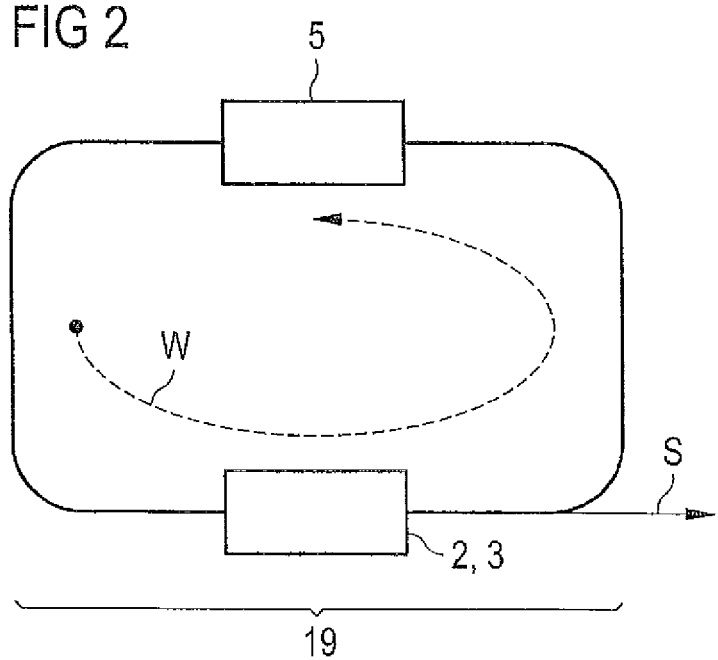

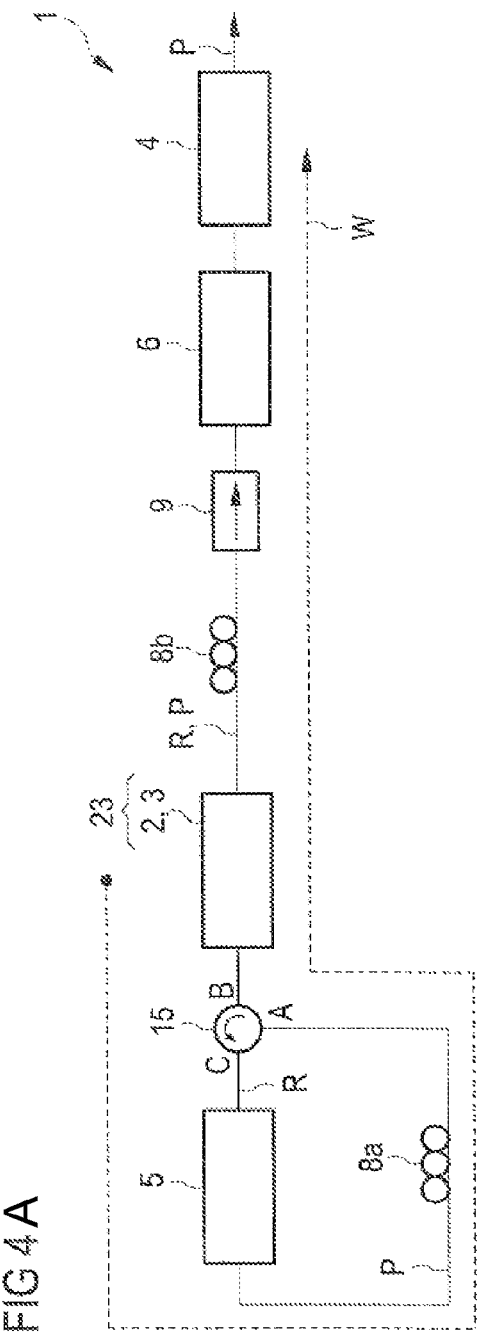
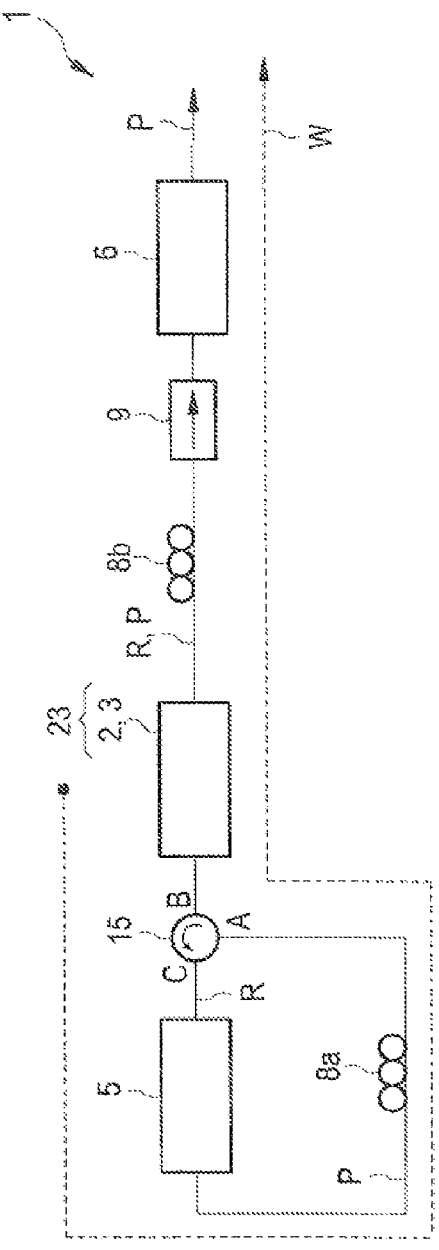

WAVELENGTH-TUNABLE LIGHT SOURCE

CROSS REFERENCE TO RELATED APPLICATIONS

This is a national phase application under 35 U.S.C. §371 of International Application No. PCT/EP2009/061419, filed on Sep. 3, 2009, which claims priority to and the benefit of German Patent Application No. 10 2008 045 634.9, filed on Sep. 3, 2008, the entire disclosures of each of which are incorporated by reference herein.

A wavelength-tunable light source is disclosed.

Spectrally narrowband, wavelength-tunable light sources are used, for example, in medicine, in particular in optical coherence tomography. Two-dimensional or three-dimensional images, for example, of human tissue, may be generated via optical coherence tomography. An important aspect of such images is the achievable resolution, i.e., inter alia, the number of pixels which result in an image. The quality of an image and its diagnostic usability are decisively influenced in this way, for example. In addition to a high detail reproduction, the period of time which is required for the generation of an image is also significant. In order to reduce the strain on a patient, for example, the period of time required for generating an image is to be reduced as much as possible. The combined requirements of high resolution and low duration mean that a high data rate is to be made possible. This places high requirements in particular on a light source usable for a tomographic method.

One possibility for implementing a narrowband, tunable light source comprises subsequently filtering a spectrally broadband radiation which is emitted by an incandescent lamp or arc lamp, for example. However, high radiation power is not achievable after the passage through the filter through this method. If the light source has a bandwidth of 100 nm and the filter has a bandwidth of 0.1 nm, for example, the loss due to the filter is approximately 99.9%, corresponding to an attenuation by a factor of 1000.

A tunable laser forms a further possibility for implementing a tunable light source. The laser has a laser medium, a resonator, and a tunable optical filter for this purpose. The laser medium can perform broadband spectral amplification. The tunable filter is situated in the resonator. Thus, only light which passes the optical filter and reaches the amplifier medium is amplified by the amplifier medium. Because a laser is based on amplification of the spontaneous emission, the radiation emitted by the amplifier medium is fed back in respect to the radiation reaching the amplifier medium. The tuning speed of the filter is a function, in addition to other factors, of the length of the resonator in particular. The greater the length of the resonator, the lower the achievable tuning speed. A reduction of the resonator length can cause increased intensity noise of the laser, however, and result in a greater frequency spacing of the modes of the laser. The maximum measuring range can be limited in applications of optical coherence tomography, abbreviated as OCT, in this way.

Another possibility for implementing a tunable light source comprises a Fourier domain mode-locked laser, abbreviated as FDML laser. Such a laser has an amplifier medium and at least one tunable filter in a resonator having a great length. The tuning speed of the filter is adapted to the length of the resonator for this purpose. In other words, the filter is transmitting again at a specific wavelength after a time which the light of this wavelength requires to pass through the resonator once. Because of this functional principle and the high speed of light, typical FDML lasers have resonator lengths in the range of multiple hundreds of meters up to several kilometers. Limitations of such an FDML laser in regard to compactness and accessible wavelength range result therefrom.

A method and an apparatus for optical coherence tomography using swept-frequency light sources are disclosed in the publication US 2008/0165366 A1.

One object to be achieved comprises disclosing a wavelength-tunable light source having a high tuning speed.

According to at least one embodiment of the light source, it has an output source, which is capable of generating electromagnetic radiation in operation. The radiation generated by the output source preferably has a large spectral width. The output source can be a semiconductor component, which displays a spectrally broadband, spontaneous emission. Rare earth-doped fibers, laser media based on solids, or Raman emitters are also suitable for use as the output source.

According to at least one embodiment of the light source, it has a wavelength-selective first filter element. The first filter element is particularly situated optically downstream from the output source. "Situated downstream" means that radiation emitted by the output source reaches the filter element. The filter element has a filtering effect with respect to the radiation emitted by the output source. i.e., the predominant part of the radiation emitted by the output source outside a specific spectral range cannot pass the first filter element. "Predominant" means that more than 80%, preferably more than 96% of the radiation outside this spectral range cannot pass the first filter element.

According to at least one embodiment of the light source, it has a first amplifier medium. The first amplifier medium is particularly situated optically downstream from the first element. i.e., radiation which passes the first filter element reaches the first amplifier medium. The first amplifier medium is capable in operation of at least partially amplifying the radiation which passes the first filter element and reaches the first amplifier medium. The first amplifier medium is, for example, a semiconductor optical amplifier, abbreviated as SOA.

According to at least one embodiment of the light source, it has at least one wavelength-selective second filter element. The second filter element is particularly situated optically downstream from the first amplifier medium. Radiation which has passed through the first amplifier medium thus reaches the second filter element. Only the radiation which was amplified by the first amplifier medium preferably reaches the second filter element. In this case, amplified means in particular that a spectral power density after passing through the first amplifier medium is higher than a spectral power density of the medium before passing through the first amplifier medium.

According to at least one embodiment of the first and/or at least one second filter elements, the wavelength-selective, filtering effect of the second filter element is based on absorption, reflection, or diffraction. For example, the filter element transmits radiation in a specific wavelength range, while radiation having other wavelengths is reflected, absorbed, and/or diffracted.

According to at least one embodiment of the light source, first element and second filter element have an optical spacing L to one another. The optical spacing L means the path length of the radiation which it has to pass through in the light source to reach the second filter element from the first filter element. The optical index of refraction of a medium which the radiation passes through on the path from the first filter element to the second filter element is to be considered in this case. The optical spacing L is thus in particular the integral over light path and index of refraction.

According to at least one embodiment of the light source, it has a control unit. The first and the at least one second filter elements are tunable via the control unit. i.e., the wavelength and/or the wavelength range in which radiation can pass the first and the at least one second filter elements can be set and tuned via the control unit. The control unit can comprise a frequency generator and/or a frequency modulator.

According to at least one embodiment of the light source, the first and the at least one second filter elements are passable by partial radiation of the radiation emitted by the output source. It is possible that first and second filter elements are passable for partial radiation in the same spectral range, in the scope of the production and measuring precision. In other words, the partial radiation thus comprises at least one specific partial wavelength range of the wavelength range emitted by the output source. The partial radiation can preferably be amplified and/or tuned over at least 50%, in particular over at least 75% of the wavelength range emitted by the output source.

According to at least one embodiment of the light source, first and second filter elements are tunable via the control unit so that first and second filter elements are transparent to the partial radiation in a time delay T to one another. The time delay T is equal in this case to the quotient of the optical spacing L and the speed of light in vacuum c, whereby c=299,792.458 km/s. Thus:

$$T = L/c.$$

In other words, the control unit tunes the filter element so that partial radiation in a specific wavelength and/or in a specific wavelength range, which passes the first element and reaches the second filter element after a runtime, is also transmitted by this second filter element. The time delay T thus corresponds to the runtime of the light in the light source from the first filter element to the second filter element. If the light source comprises more than one second filter element, preferably all further filter elements are tunable in a corresponding manner by the control unit.

According to at least one embodiment of the light source, a tolerance or a variation for the setting of the time delay T is small enough that the wavelength range transmitted by the first filter element corresponds at least 0.1%, preferably at least 5%, particularly preferably at least 30%, to the wavelength range transmitted by the at least one second filter element. Considering the time delay T, the wavelength ranges transmitted by the first and the at least one second filter elements correspond at least in the amount of the cited values.

According to at least one embodiment of the light source, the time delay T is varied in relation to the quotient of L/c, so that the time delay T is less or greater than the quotient of L/c. This variation is at most large enough in this case that a central wavelength of a filter transmission of the second filter element deviates from a central wavelength of the partial radiation by at most a factor of 10, preferably by at most a factor of 1, particularly preferably by at most a factor of 0.5 times a filter bandwidth of the second filter element. The filter bandwidth is the full spectral width at half the height of a maximum transmission, for example, abbreviated as FWHM. For example, if the central wavelength of the partial radiation applied to the second filter element is 1320 nm and the filter bandwidth is 1 nm at a specific point in time, the central wavelength of the filter transmission of the second filter element is between 1310 nm and 1330 nm inclusively, preferably between 1319 nm and 1321 nm, particularly preferably between 1319.5 nm and 1320.5 nm. Through a variation of the time delay T of this type it is possible, for example, to set the wavelength range of the partial radiation exactly.

To improve filter properties of a filter element, for example, two directly sequential filters may be combined into one filter element. This is the case, for example, in the event of vernier tuning.

In at least one embodiment of the wavelength-tunable light source, it comprises an output source which is capable of generating electromagnetic radiation in operation. Furthermore, the light source has a wavelength-selective first filter element, which is situated downstream from the output source. In addition, the light source contains a first amplifier medium, which is situated downstream from the first filter element and is capable of at least partially amplifying the radiation emitted by the output source. The light source further comprises at least one wavelength-selective second filter element, which is situated downstream from the amplifier medium, the second filter element having an optical spacing L to the first filter element. The first and the at least one second filter elements are tunable via a control unit which the light source has. The filter elements are tuned in this case so that first and second filter elements are transparent in a time delay T to one another for a partial radiation of the radiation emitted by the output source, the delay T being equal to the quotient of the optical spacing L and the speed of light in vacuum c.

Such a wavelength-tunable light source allows high tuning speeds to be achieved in respect to the wavelength of the partial radiation emitted by the light source. Spectrally narrowband partial radiation can also be emitted by the light source.

Such a light source is based, inter alia, on the following findings: The output source generates electromagnetic radiation which covers a certain frequency range in operation of the light source. A part of the radiation in the frequency range passes the first filter element and reaches the first amplifier medium. The spectral component emitted by the first filter element is amplified in the first amplifier medium. To suppress radiation which has wavelengths different from the partial radiation, the light emitted by the amplifier medium subsequently passes through a second filter element. i.e., at least two filter elements are situated cascaded or in series. First and second filter elements have an optical spacing L to one another. Due to this optical spacing L, light of the partial radiation which passes through the first filter element only reaches the second filter element after a specific time delay. If first and second filter elements are tuned synchronously with one another, i.e., first and second filter elements are transmitting simultaneously for a specific spectral range, for example, it can occur that the partial radiation which has passed through the first filter element can no longer pass the second filter element, because it is already tuned to another spectral range. In the event of an activation of the filter elements of this type, the tuning speed at which the wavelength of the partial radiation can be tuned is thus limited. Because first and second filter elements are passable by a specific spectral range with a time delay, this limitation is dispensed with. The time delay T with which the filter elements are tuned corresponds to the runtime difference which the partial radiation experiences on the path from the first filter element to the second filter element.

According to at least one embodiment of the light source, it does not have a resonator having an amplifier medium. i.e., an amplifier medium which is pumped is located inside the resonator, for example, as in a laser. Components which are used for frequency filtering and are based on the Fabry-Perot principle are not resonators in this definition. For example, in a laser, the resonator is an element which is decisive for the mode of operation of the laser.

According to at least one embodiment of the light source, it comprises at least one second amplifier medium. The second amplifier medium is preferably based on a semiconductor medium. The second amplifier medium is particularly an SOA. The radiation power emitted by the light source can be increased by the use of a second amplifier medium.

According to at least one embodiment of the light source, the output source is usable as an amplifier medium, in particular as the first amplifier medium. This means that the light emitted by the output source reaches the first filter element, passes the filter element, and subsequently passes through the output source again. The previously filtered light is amplified when passing through the output source again.

In such a construction of the light source, the first amplifier medium is also situated downstream from the first filter element in respect to the run path of the light. By also using the output source as an amplifier medium, a particularly compact light source can be constructed.

According to at least one embodiment of the light source, the partial radiation can pass through at least one filter element and/or at least one amplifier medium at least twice. In other words, the partial radiation which has passed through the first filter element, for example, and comprises a partial wavelength range of the radiation emitted by the output source, is guided in the light source so that this partial radiation reaches the first filter element a further time or passes through the first and/or second amplifier media at least twice. Through such radiation guiding in the light source, the number of components of the light source may be reduced. A more compact and cost-effective construction of the light source is made possible in this way.

According to at least one embodiment of the light source, the partial radiation can pass through at least one filter element and/or at least one amplifier medium at least four times. A particularly large number of components may be saved and the compactness of the light source can be increased by such guiding of the partial radiation inside the light source.

According to at least one embodiment of the light source, it comprises at least two polarization-selective elements. At least one polarization-selective element is, for example, a polarizer, a Brewster window, or a polarization-dependent reflecting beam splitter. Through the use of such an element it is possible to have the partial radiation pass through components of the light source multiple times efficiently.

According to at least one embodiment of the light source, it comprises at least one first and/or second amplifier media, which are designed as polarization-dependent. This means that only partial radiation of a specific polarization direction is efficiently amplified by the amplifier medium. Through such an amplifier medium it is possible that the polarization properties of the light emitted by the light source are intentionally settable.

According to at least one embodiment of the light source, it has at least two polarization-selective elements, the first and/or the second amplifier media being amplifying polarization-independent. In this way it is made possible that light of different polarization directions is deflected through an amplifier medium via the polarization-selective elements and nonetheless experiences amplification in the amplifier medium. This simplifies the construction of the light source.

According to at least one embodiment of the light source, it is wavelength-agile. Wavelength-agile, or equivalently thereto frequency-agile, means that the light source provides a spectrally narrowband radiation and various wavelengths or wavelength ranges of the partial radiation are settable in a rapid and controllable manner. In this way, limited solely by the spectral width of the radiation generated by the output source and by the maximum tuning speed of the filter elements, arbitrary waveforms and time curves of the wavelength of the partial radiation may be generated. These differentiate the light source, for example, from a laser having a resonator or from an FDML laser, in which the wavelength time curve of the emitted radiation is extensively predetermined by the construction of the laser.

According to at least one embodiment of the light source, it is non-periodically tunable. This means that the time curve of the wavelength of the partial radiation for which the filter elements are passable has no periodicity. This means that within a specific time, which is significantly greater than a circulation or passage time of the light through the light source, the time curve of the wavelength of the partial radiation does not repeat or does not repeat periodically. The light source is preferably non-periodic within a time range of at least 100 µs, in particular at least 10 ms or at least 1 s. Because the light source is non-periodically tunable, the possible uses of the light source are increased.

According to at least one embodiment of the light source, the output source, the at least one amplifier medium, and the filter elements are at least partially, preferably completely optically connected to one another via optical fibers. The optical fibers may be implemented as glass fibers, for example. The stability of the light source, in particular in relation to environmental influences, is increased by the use of optical fibers.

According to at least one embodiment of the light source, the first filter element and/or the at least one second filter element are implemented using a fiber-Fabry-Perot filter. Such a filter comprises, for example, the ends of two diametrically opposite optical fibers, the ends implementing a Fabry-Perot element. The ends may be reflective. The spacing between the ends, and thus the wavelength range to be transmitted, can be set via a piezo-actuator. Filters of this type have compact constructions and may be tuned at higher tuning speed. All filter elements are preferably implemented as fiber-Fabry-Perot filters.

According to at least one embodiment of the light source, the first filter element and/or the at least one second filter element is a transmissive-absorptive filter. That is to say, the partial radiation is transmitted and the remaining radiation is essentially absorbed. The absorption of the non-transmitted partial radiation is preferably greater than 80%, in particular greater than 90%. Through the use of such a filter, radiation having wavelengths other than the partial radiation can be efficiently suppressed.

According to at least one embodiment of the light source, the first filter element and/or the at least one second filter element comprises at least one optical grating or an optical prism and/or a polygonal mirror. The use of such components for at least one filter element increases the possible designs of the light source and allows manifold possible uses of the light source.

According to at least one embodiment of the light source, at least one first and/or second amplifier media are usable as the filter element. That means, for example, the spectral range in which the amplifier medium displays an amplification of radiation is spectrally narrow. In other words, only radiation in a narrow spectral range is amplified by the amplifier medium. It is also possible that a filtering effect with respect to a spectral range is generated via pumping of the amplifier medium in the time domain, in particular if the partial radiation, which is applied to the amplifier medium and is to be amplified, displays a time curve with respect to its wavelength. In this case, for example, the amplifier medium is only electrically pumped in specific time ranges, for example.

Radiation can only be amplified during this time range, in which the amplifier medium is pumped. If the amplifier medium is formed using a semiconductor component, the spectral range in which the amplifier medium displays amplification can alternatively or additionally be set by a strength of the current with which the amplifier medium is supplied. A compact light source can be implemented by such a design of an amplifier medium.

According to at least one embodiment of the light source, the spectral width of the radiation emitted by the output source is at least 20 nm. In other words, the output source displays a spontaneous emission in a spectral range of at least 20 nm, for example. The spectral width of the radiation is preferably at least 70 nm, in particular at least 100 nm. A spectrally broadband output source of this type increases the possible uses of the light source and allows a high resolution in the field of optical coherence tomography.

According to at least one embodiment of the light source, a spectral width of the partial radiation is in the value range between 0.003 nm and 5 nm, in particular between 0.05 nm and 1 nm. Thus, for example, the filter elements have a transmission range which corresponds to the spectral width of the partial radiation. A low spectral width of the partial radiation allows a high spectral resolution to be achieved using the light source.

According to at least one embodiment of the light source, an optical coherence length of the partial radiation is at least 3 mm. The coherence length is preferably at least 5 mm. This means that the partial radiation implements wave trains, whose length at least corresponds to the coherence length, and the partial radiation is capable of interference within this length. The coherence length determines, inter alia, a maximum depth, up to which recordings may be generated in tissue, for example, in the context of optical tomography. More expensive structures may also be studied via such a coherence length in the context of a tomographic application.

According to at least one embodiment of the light source, a central wavelength of the partial radiation is tunable during the time delay T by at least one-tenth of the spectral width of the partial radiation. The central wavelength is preferably tunable by at least the spectral width of the partial radiation. High data rates in the context of a tomographic application, for example, are achievable by such a light source.

According to at least one embodiment of the light source, a tuning speed of at least one of the filter elements is at least temporarily at least 0.5 nm/µs. The tuning speed is preferably at least 3.0 nm/µs. Such a tuning speed is preferably achievable for all filter elements. High data rates can be implemented via a light source having tuning speeds this high, for example, in the context of a tomographic application.

According to at least one embodiment of the light source, a tuning frequency of the at least one filter element, using which the wavelength of the partial radiation is tuned, is at least temporarily at least 40 kHz. The tuning frequency is preferably at least 80 kHz, particularly preferably at least 150 kHz. The filter element can particularly be tuned periodically, for example, in the form of a sine wave or sawtooth, using such a frequency. Such a light source can be used in manifold ways in coherence tomography.

According to at least one embodiment of the light source, its optical length is less than or equal to 300 m. The optical length is preferably less than or equal to 30 m. Optical length is to be understood as the path length of the light which the light covers from the generation in the output source up to leaving the light source. The particular index of refraction of the medium which the light passes through is to be considered for this purpose. Such a light source has a compact construction and allows use in manifold spectral ranges.

According to at least one embodiment of the light source, its optical length is greater than 10 cm, preferably greater than 50 cm, in particular greater than 1 m.

According to at least one embodiment of the light source, at least the first and/or the at least one second amplifier media contain at least one optical semiconductor amplifier. Preferably, all amplifier media, in particular all amplifier media and the output source, are implemented having a semiconductor amplifier. A compact and reliable light source can be implemented by such amplifier media.

According to at least one embodiment of the light source, at least the first and/or the at least one second amplifier media contain at least one rare-earth-doped glass fiber or are formed by such a fiber. It is possible that all amplifier media, in particular the output source, comprise such a glass fiber.

According to at least one embodiment of the light source, at least one first and/or second amplifier media can be powered in a tunable manner. In particular, the amplifier medium can be powered synchronously to the spectral tuning of the filter elements. Through a tunable powering of the amplifier medium, a uniform output power in respect to the partial radiation of the light source can be ensured.

According to at least one embodiment of the light source, the output source is a semiconductor optical amplifier and the first and/or the at least one second amplifier media are a rare-earth-doped glass fiber. A wavelength of the radiation emitted by the light source is preferably between 1000 nm and 1200 nm inclusive. High optical powers of the light source may be achieved by a use of radiation sources of various types in the light source. Particularly small variations in the power of the radiation emitted by the output source are also achievable, and pulsed operation, which can be undesirable, can be suppressed. Spectral forming of the radiation can also be made possible by variable powering of the output source.

According to at least one embodiment of the light source, the following relationship applies for a saturation power $P_{sat}$ of the first and/or the second amplifier media:

$$P_{sat} > 0.1 G P_A (B_P/B_A).$$

For this purpose, G is a small amplification factor of the first and/or the second amplifier media, $B_P$ is the spectral width of the partial radiation, and $B_A$ stands for the spectral width of the radiation emitted by the output source. $P_A$ is a total power of the radiation of the output source. The above context is preferably fulfilled if the first amplifier medium and the output source are formed by the same element. Through such a saturation power $P_{sat}$ of the first amplifier medium, it is made possible for the partial radiation to be tunable over a wide spectral range of the radiation emitted by the output source.

According to at least one embodiment of the light source, $P_{sat}$ is at least one time, preferably at least five times as great as the product of small amplification factor G, spectral width $B_P$ of the partial radiation divided by spectral width $B_A$ of the radiation, and the total power $P_A$ of the radiation of the output source.

According to at least one embodiment of the light source, it comprises at least one detector, preferably a wavelength-selective detector. The detector, such as a photodiode, is only sensitive in a specific spectral range via a color filter or an interference filter, for example. The detector is preferably only accessible to the radiation emitted by the output source for a small spectral range. The light emitted by the light source can be characterized by such a detector.

According to at least one embodiment of the light source, the control unit is connected to the at least one detector and the delay T is settable by a signal of the detector. i.e., the control unit receives and processes the wavelength-selective signal of the detector. The time delay T is automatically settable in particular via the control unit and such a detector.

According to at least one embodiment of the light source, the detector detects a component of the partial radiation which was reflected by a second filter element. The setting of the time delay T can be automated and can be performed more easily via such a detector.

According to at least one embodiment of the light source, it comprises at least one shutter. The light emission of the light source can be temporarily prevented via the shutter. Therefore, no light exits from the light source during time intervals defined via the shutter. The shutter can comprise one or more filter elements. The shutter is preferably also activated by the control unit. It is possible that an activation of the shutter occurs synchronously to the activation of the filter elements, for example. The light source is increased in its possible uses by the employment of a shutter.

According to at least one embodiment of the light source, it is capable of emitting partial radiation in the near-infrared spectral range. That is to say, the partial radiation emitted by the light source comprises wavelengths in the spectral range between 780 nm and 3000 nm, in particular between 1000 nm and 1700 nm. The partial radiation can also exclusively comprise near-infrared light.

According to at least one embodiment of the light source, it is capable of emitting partial radiation of a wavelength of less than or equal to 900 nm, preferably less than or equal to 800 nm. Such a light source is capable of being used in ocular diagnostics, for sample. For example, FDML lasers have system-related resonator lengths of multiple hundreds of meters up to multiple kilometers. Therefore, only glass fibers and/or optical fibers having very low attenuation may be used. This does not represent a significant limitation in the wavelength ranges around 1050 nm, 1300 nm, and 1550 nm, because the attenuation of available optical fibers in this range is less than 1 dB/km. In other spectral ranges, for example, around 800 nm, the attenuation is significantly greater at 3 dB/km. In addition to the greater attenuation, the chromatic dispersion in the spectral range around 800 nm, for example, is also significantly greater than in the other above-mentioned spectral ranges. Due to the significantly lower path length of material to be passed through in comparison to FDML lasers, the light source can also emit radiation at and/or below 900 nm.

According to at least one embodiment of the light source, the optical spacing between the output source and the first amplifier medium is selected to be as great as possible. This is preferably true if the output source is used as the first amplifier medium and/or a total amplification of the radiation of the output source is at least 40 dB. Total amplification relates in this case to a double passage of the radiation through the output source used as the first amplifier medium. As great as possible can mean that the optical spacing between the output source and the first amplifier medium corresponds to at least 0.2 times the quotient of the speed of light in vacuum c and a filter changing time, in particular at least 0.3 times, preferably at least 0.5 times this quotient. The filter changing time is, for example, a period duration of the wavelength tuning, multiplied by the filter bandwidth of the filter, and divided by the spectral width of the radiation emitted by the light source.

According to at least one embodiment of the light source, it comprises at least one delay route. The delay route has a greater optical length than a bypass route, which is connected in parallel to the delay route. For example, the delay route and the bypass route are branched and/or connected to one another via fiber couplers or via beam splitters.

According to at least one embodiment of the light source, the delay route, viewed in the run direction of the radiation, is located after the last of the filter elements and preferably before the second amplifier medium.

According to at least one embodiment of the light source, the delay route, viewed in the run direction of the radiation, is located between two sequential filter elements.

Some areas of application in which a light source according to one or more of the described exemplary embodiments can be used are biomedical imaging, for example, in the fields of ophthalmology, cardiology, or gastroenterology, profilometry having sub-nanometer resolution in mechanical engineering, sensors, in particular the readout of fiber Bragg gratings, distributed temperature measurement, distributed strain measurement, in particular in the mechanical field, vector sonar, encryption of an optical communication line, or monitoring/management of telecommunication networks.

A light source described here is explained in greater detail hereafter on the basis of exemplary embodiments. Identical reference numerals specify identical elements in the individual figures. However, references are not to scale, rather individual elements may be shown exaggeratedly large for better understanding.

Figure 5:
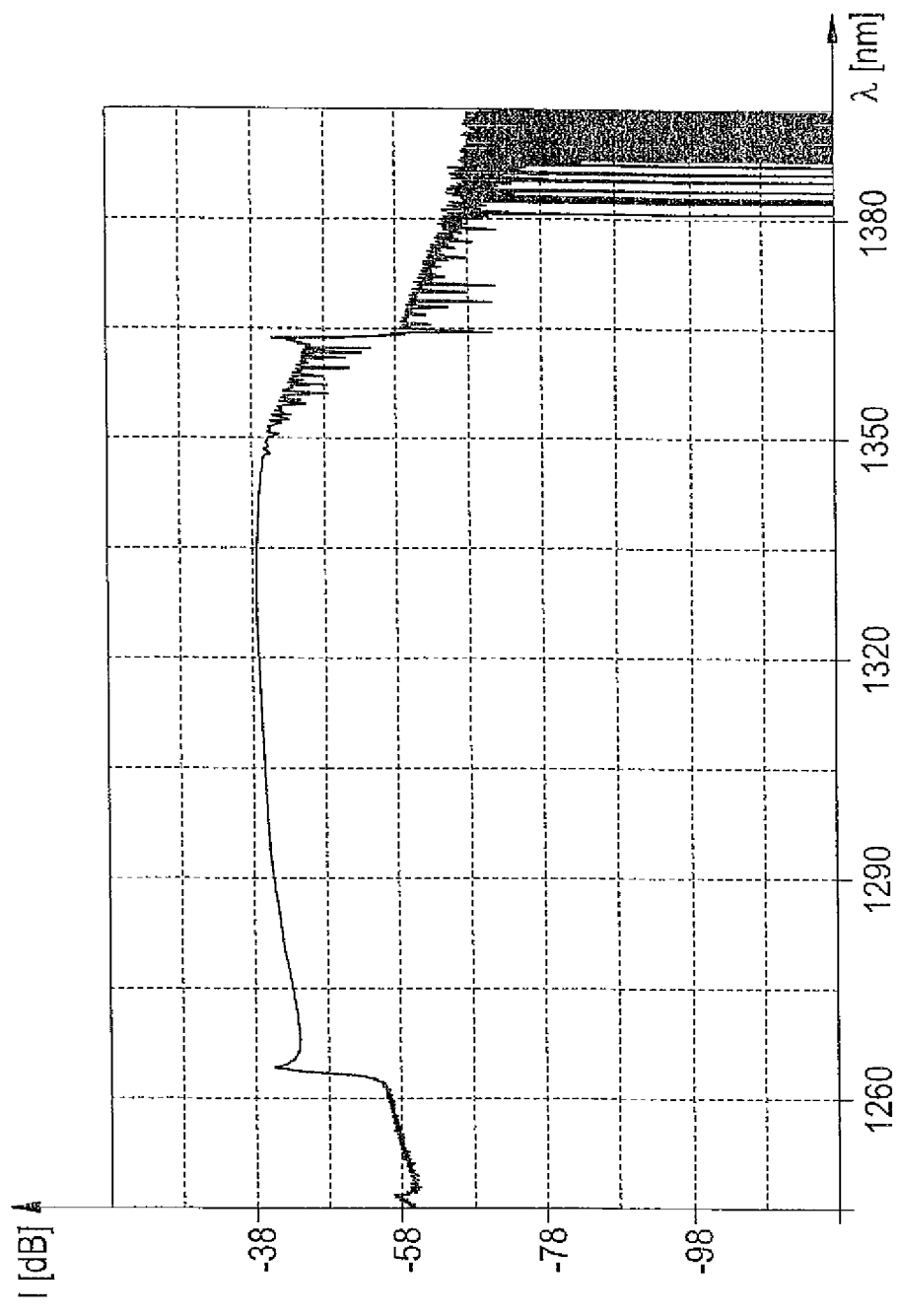
Figure 6:
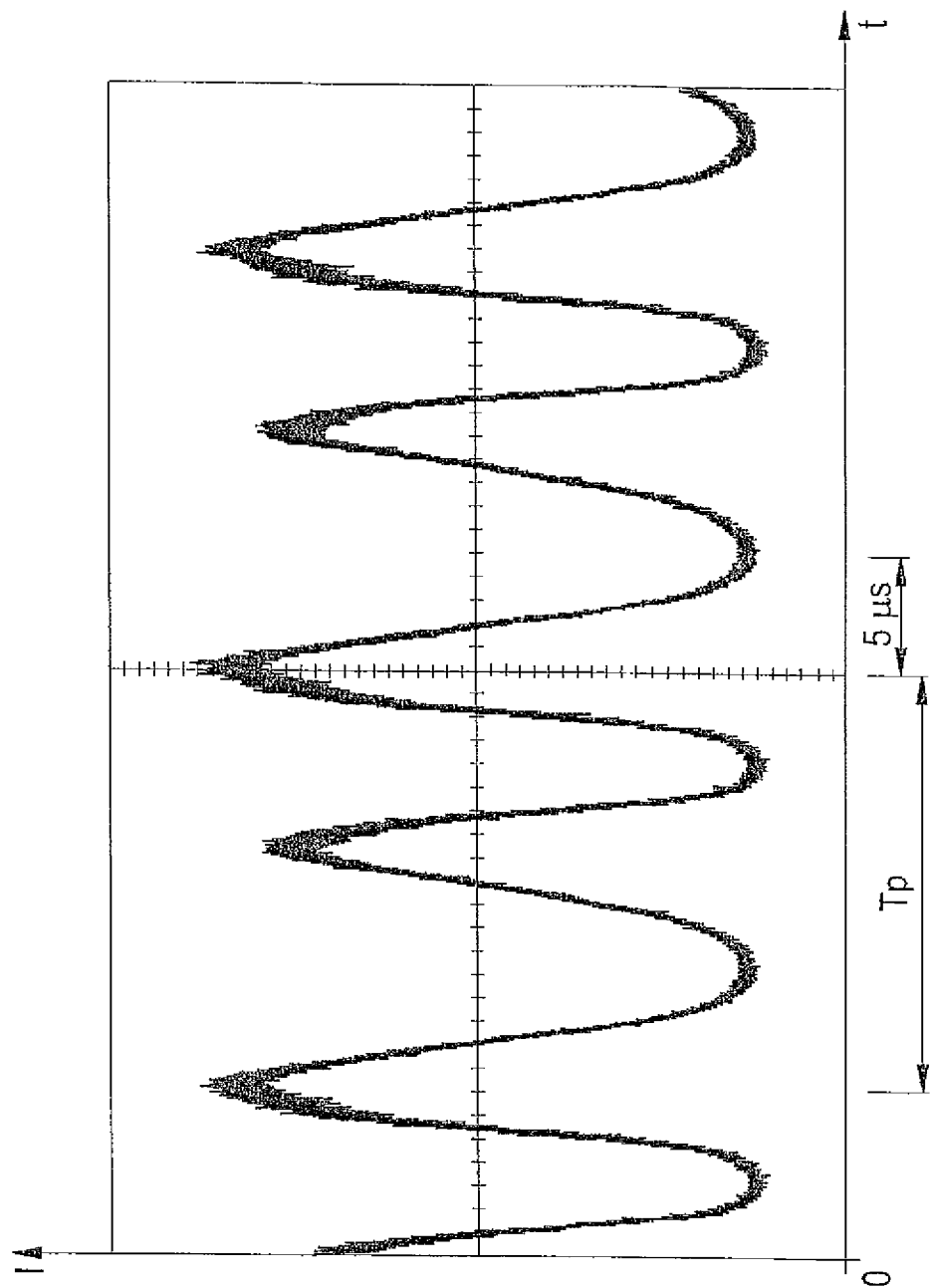
Figure 7:
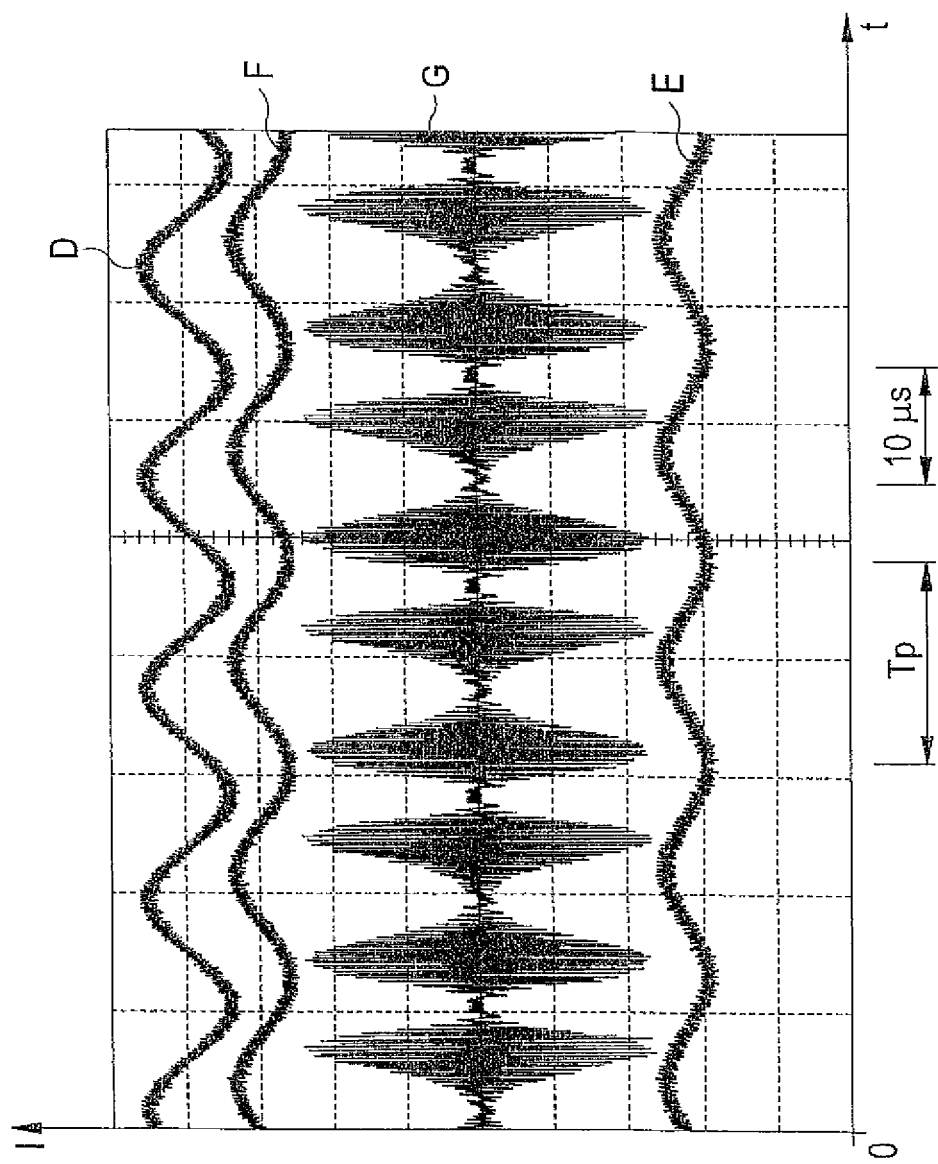
Figure 8:
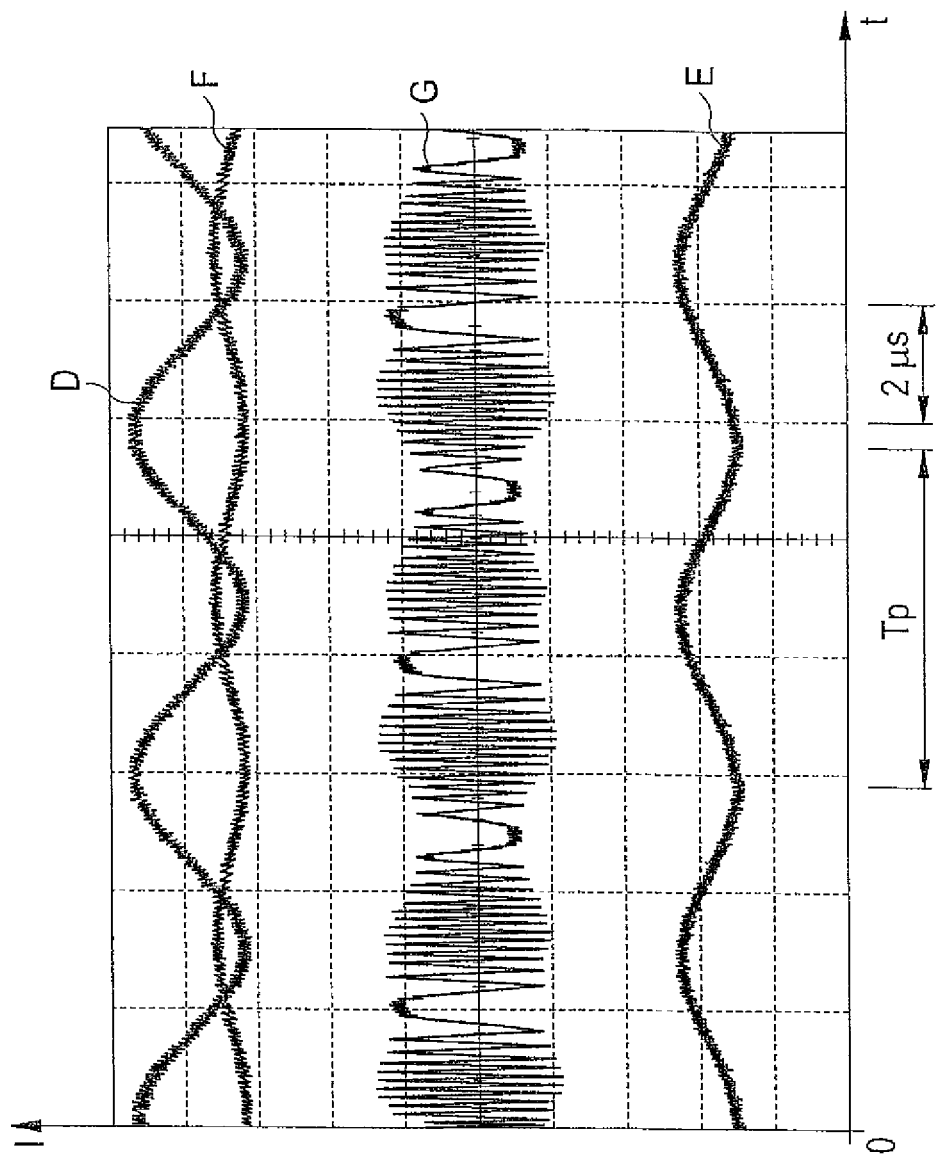
Figure 9:
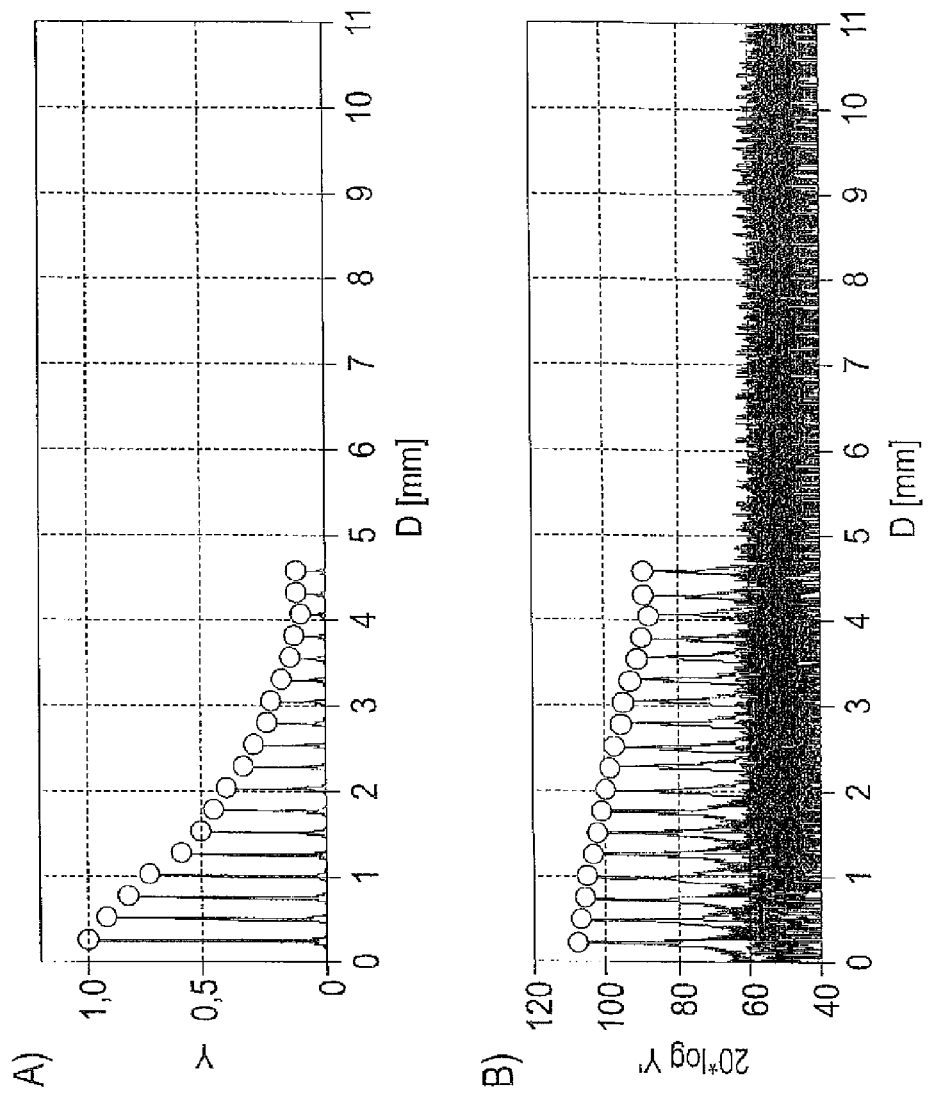
Figure 18:
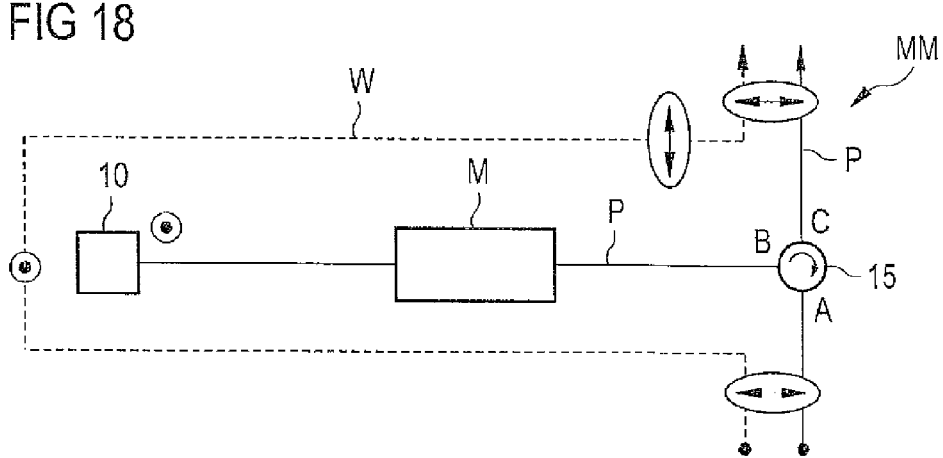
Figure 19:
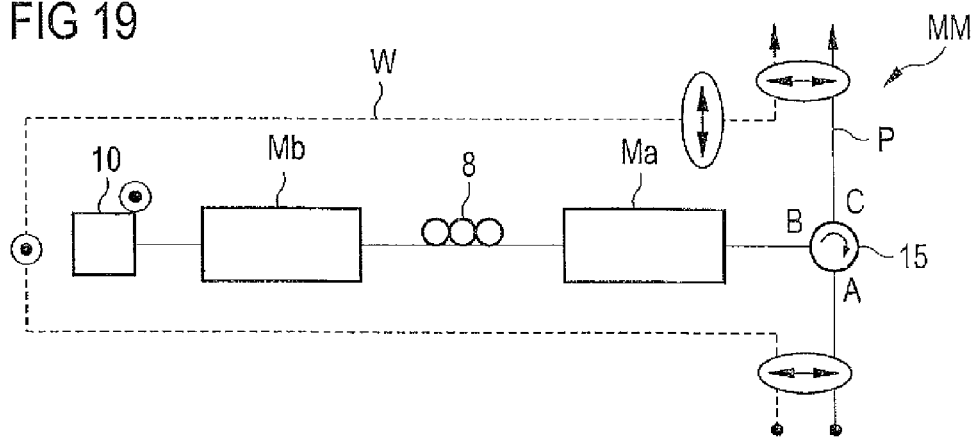
Figure 20:
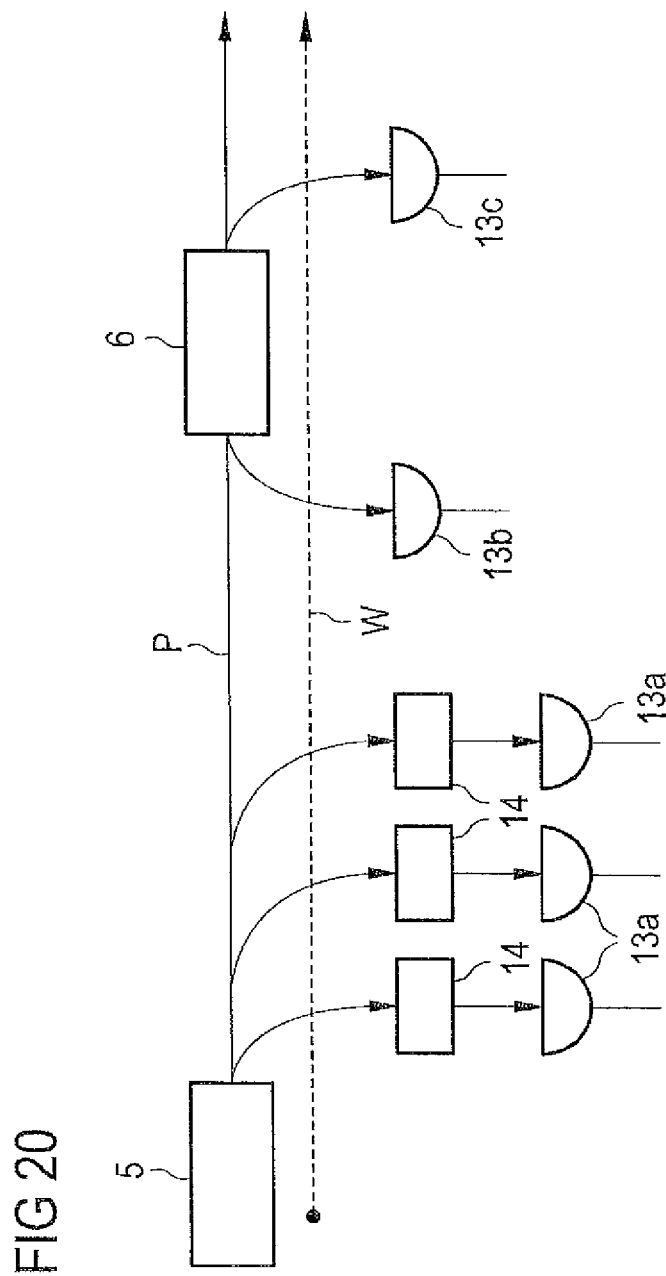
Figure 21:
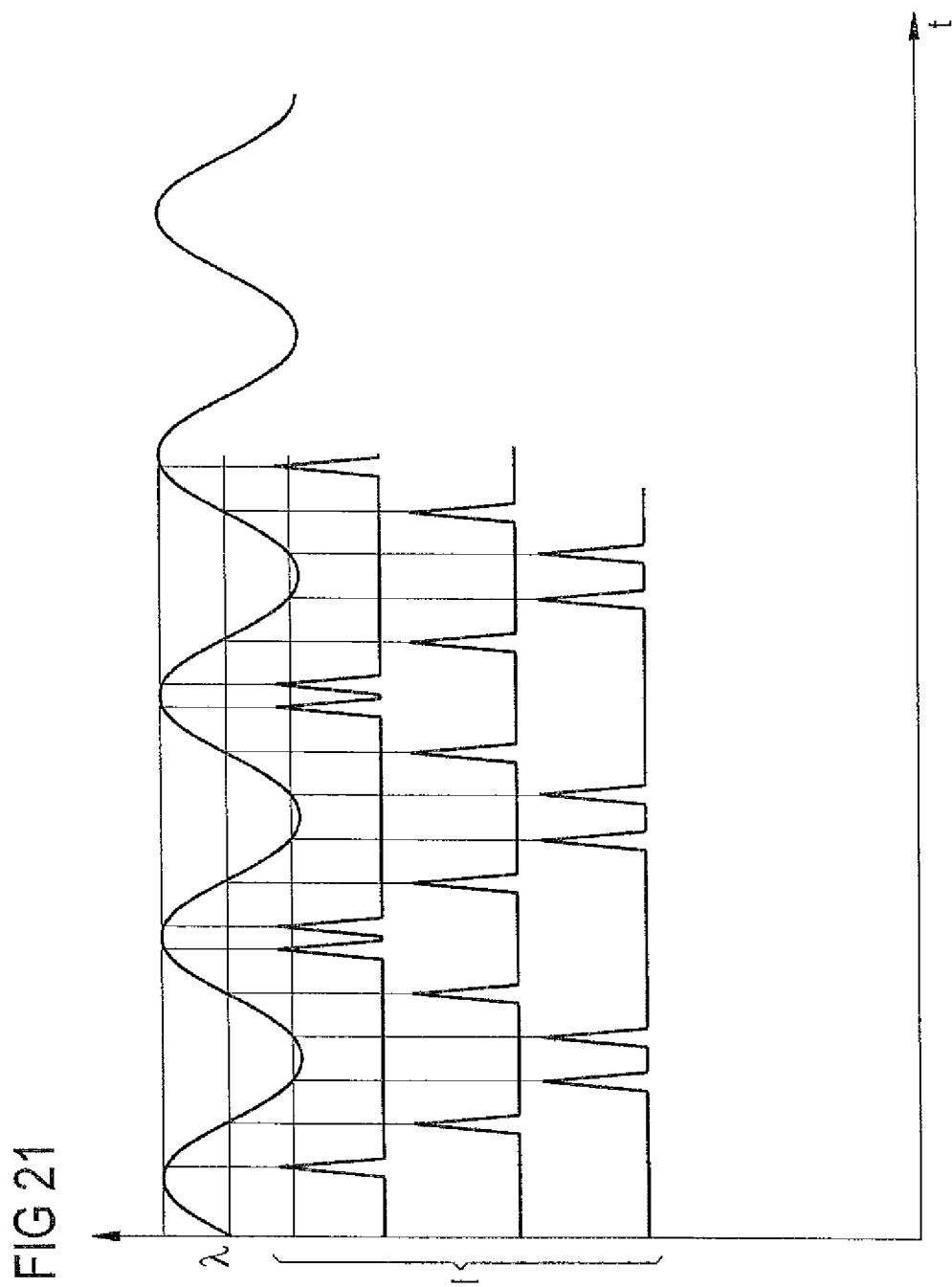
Figure 22:
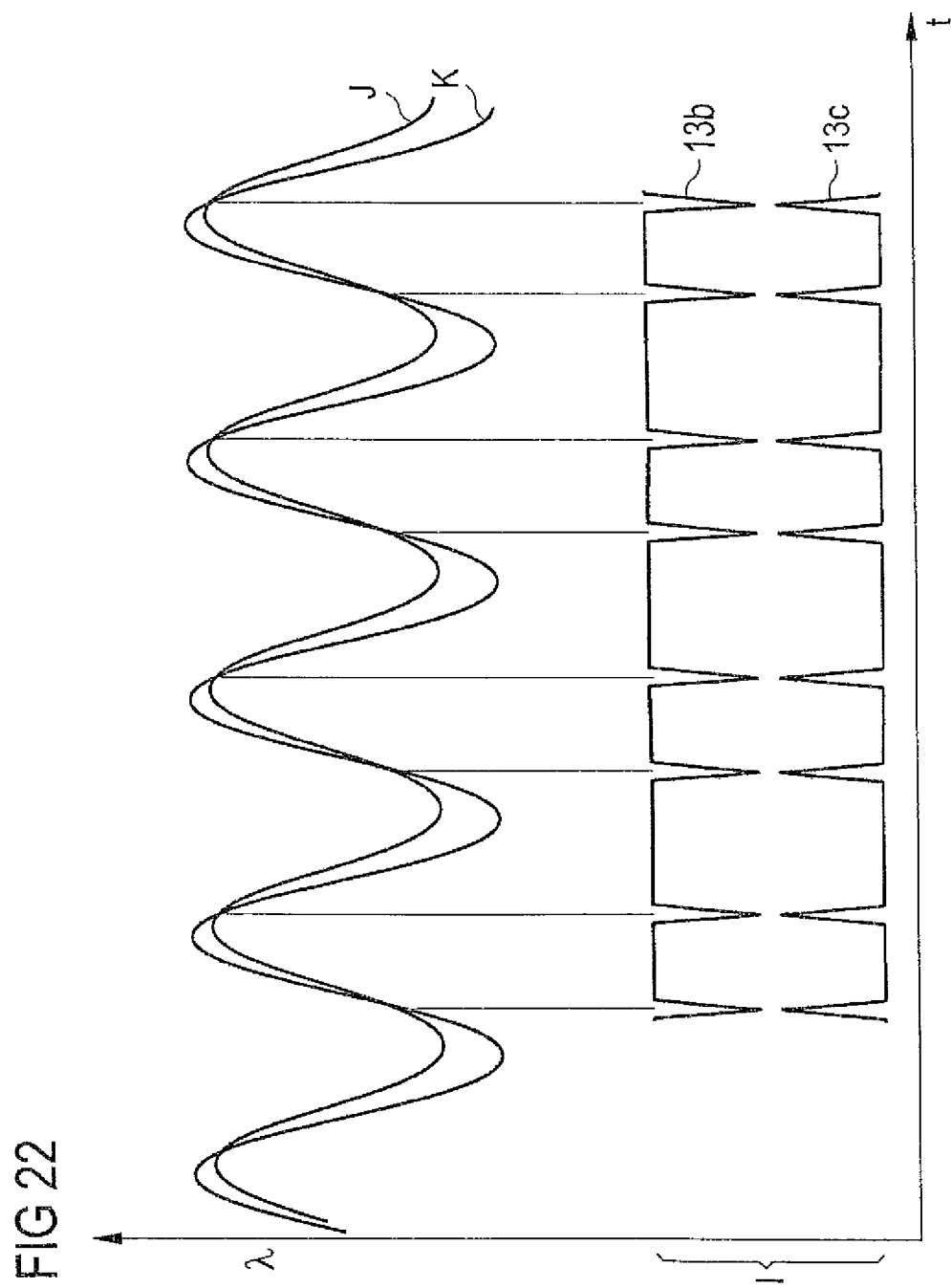
Figure 23:
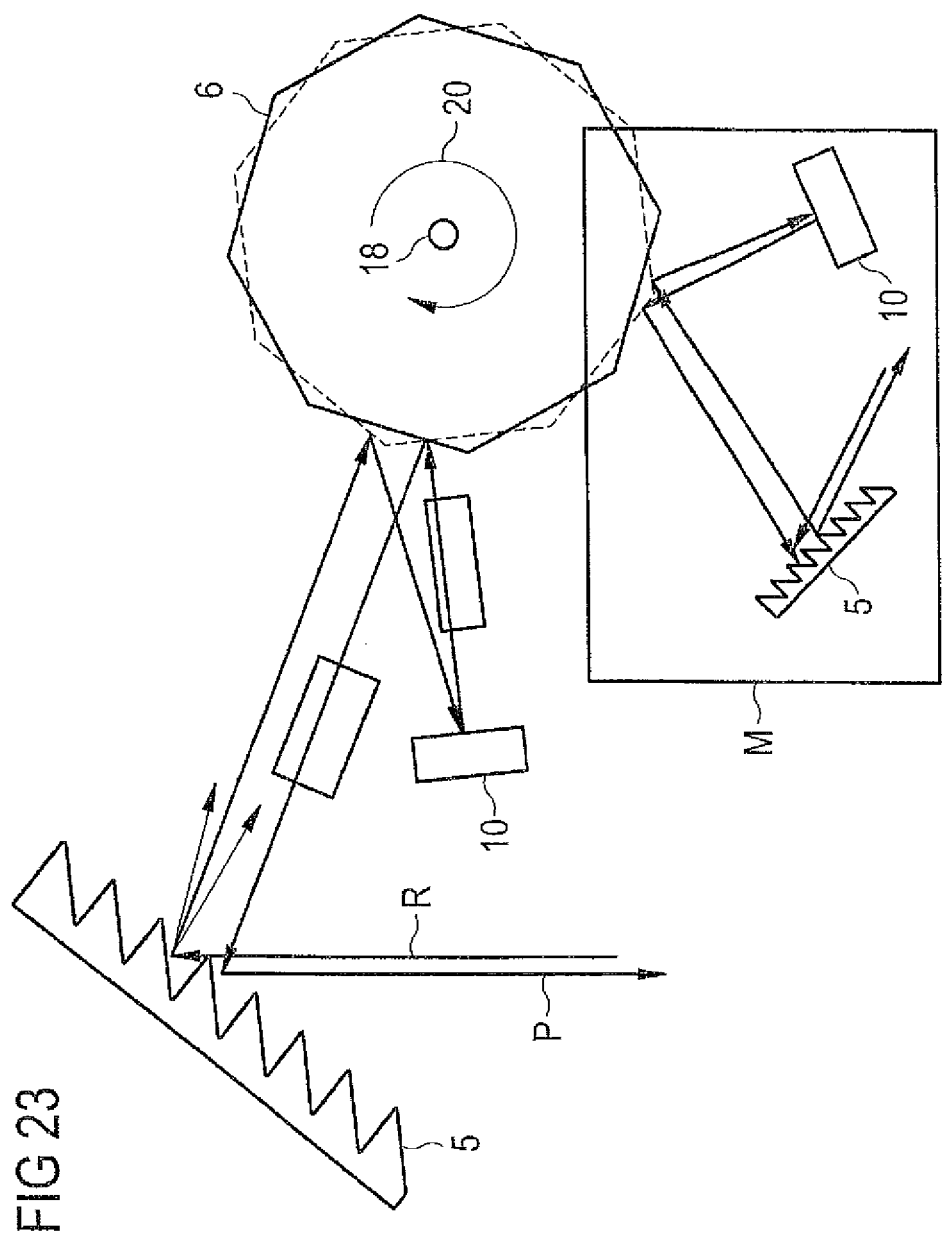
Figure 24:
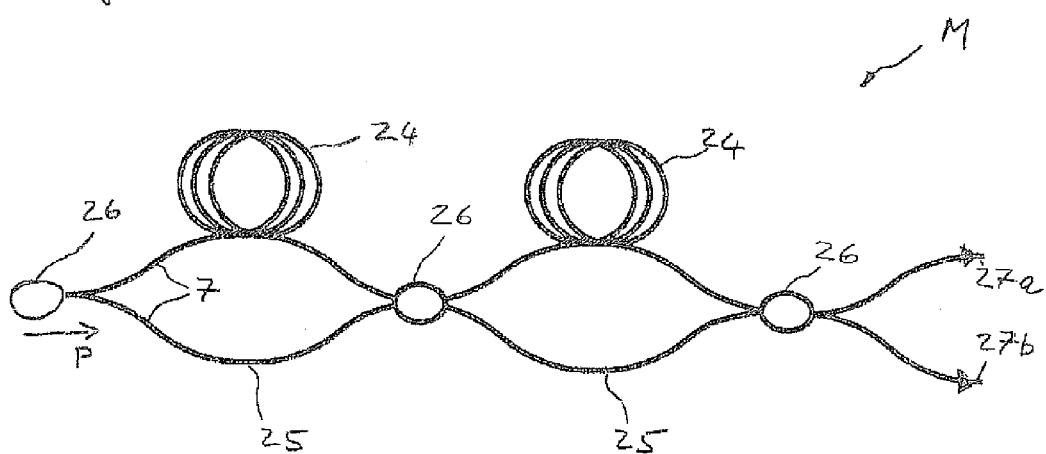
Figure 25:
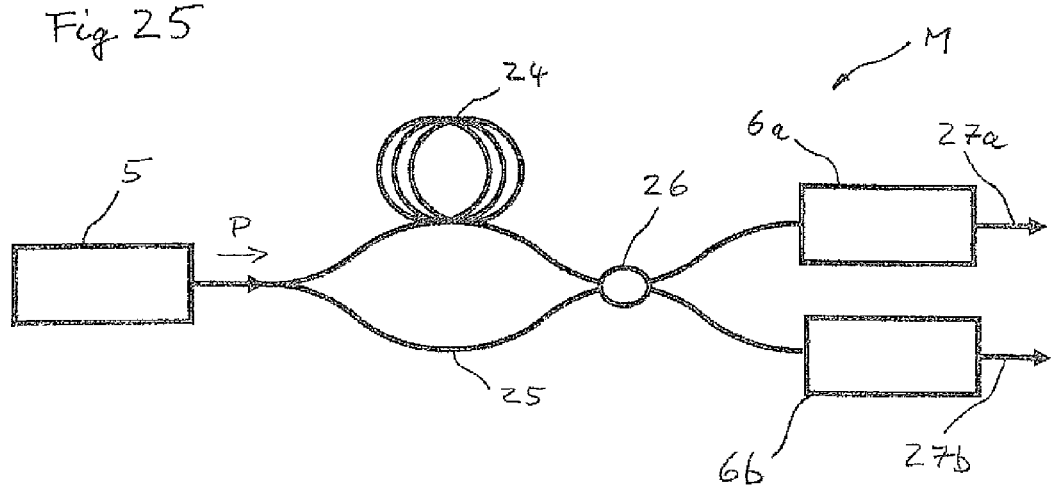

In the figures:

FIGS. 1A and B show schematic illustrations of exemplary embodiments of the light source described here, without and with optional amplifier, respectively, FIG. 2 shows a schematic illustration of a tunable laser according to the prior art, FIG. 3 shows a schematic illustration of a circulation scheme of a tunable laser according to the prior art, FIGS. 4A and B show schematic illustrations of exemplary embodiments of a light source described here, in which the output source and first amplifier medium are formed by the same element without and with optional amplifier, respectively, FIG. 5 shows an illustration of a time-averaged emission spectrum of an exemplary embodiment of a light source described here, FIGS. 6 through 8 show illustrations of the output power, and the driver and interference signals of an exemplary embodiment of a light source described here, FIG. 9 shows an illustration of the mean integrated linewidth of an exemplary embodiment of the light source described here, FIGS. 10 through 19 show schematic illustrations of exemplary embodiments of light sources described here having multiple passage of the partial radiation through individual components of the light source, FIG. 20 shows a schematic illustration of the synchronization of multiple filter elements of an exemplary embodiment of a light source described here, FIGS. 21 and 22 show schematic illustrations of signals of detectors of an exemplary embodiment of a light source described here, FIG. 23 shows a schematic illustration of a configuration of filter elements of an exemplary embodiment of a light source described here, and FIGS. 24 and 25 show schematic illustrations of modules for further exemplary embodiments of light sources described here.

An exemplary embodiment of a wavelength-tunable light source 1 described here is shown in FIG. 1A A spectrally broadband radiation R is emitted by an output source 2. The radiation R then passes through a first filter element 5, which is passed by a partial radiation P, which represents a part and a spectral detail of the radiation R. The partial radiation P is amplified in a first amplifier medium 3. The first amplifier medium 3 is designed so that the predominant or the entire spectral range which the radiation R of the output source covers can also be amplified in the first amplifier medium 3. The partial radiation P is thus tunable over the predominant or entire spectral range of the radiation R.

However, this is also accompanied by the circumstance that a smaller component of a spectrally broadband background radiation is also generated with the amplification of the partial radiation P. In order to suppress this interfering background radiation, a second filter element 6, which permits the amplified partial radiation P to pass, is situated downstream from the first amplifier medium 3.

First filter element 5 and second filter element 6 have an optical spacing L to one another. Both filter elements 5, 6 are wavelength-tunable, the tuning occurs via the control unit 11. A driver signal, symbolized by two different double lines, which is applied to the first element 5, is applied to the second filter elements 6 with a time delay T, which corresponds to the optical spacing L divided by the speed of light in vacuum c. The runtime difference of the partial radiation P on the path from the first filter element 5 to the second filter element 2 [sic; 6], which is approximately 5 ns for a run path of 1 m through an optical fiber, is thus compensated for by the control unit 11. This prevents the partial radiation P from experiencing a significant intensity reduction through sequential filter elements 5, 6 at high tuning speeds of the filter elements 5, 6 situated in a cascade.

Referring also to FIG. 1B, a second amplifier medium 4, which amplifies the partial radiation P once again, is optionally situated downstream from the second filter element 6. High output powers of the partial radiation P are thus achievable. The second amplifier medium 4 essentially has the same spectral amplification range as the first amplifier medium 3. Without the second filter element 6, the background radiation would also be amplified by the second amplifier medium 4, the partial radiation P would then only be spectrally tunable in a limited way or not at all and/or the partial radiation P would have a spectrally broad background.

A tunable laser according to the prior art is shown in FIG. 2. The laser has an amplifier medium 3, which is simultaneously used as the output source 2. The amplifier medium 3 is located, as is a filter 5, in a resonator 19, which is schematically shown as an annular structure. Radiation S generated by the laser is identified as the arrow line, a light path W of the radiation S in the resonator 19 is illustrated as a dashed arrow line. The filter 5 is implemented as a grating mirror or as a fiber-Fabry-Perot filter, for example.

A circulation time $T_U$ of the light in the resonator 19 corresponds to a resonator length $L_U$ divided by the speed of light in vacuum c, the indices of refraction of the media which the light passes through being considered in the resonator length $L_U$.

Only those wavelengths which are not absorbed by the filter 5 may circulate in the resonator 19 of the laser. In normal operation, the laser emits light having a wavelength which approximately corresponds to a loss minimum and/or a maximum of a transmission window $B_P$ of the filter 5. In order to obtain a continuously tunable laser, the wavelength of the transmission window $B_P$ of the filter 5 is changed. This method is practical as long as the light can complete multiple circulations in the resonator 19, before the transmission window $B_P$ of the filter 5 is shifted to another wavelength. A tuning speed of the filter 5 is limited by this condition.

In FIG. 3, the principle of a tunable laser according to FIG. 2 is shown in a further illustration. The cyclic passage of the radiation S through the resonator 19 is illustrated as a linear sequence. The radiation S passes through the filter element 5 and subsequently the amplifier medium 3 in a first circulation U1, symbolized in FIG. 2 by a curved bracket. Subsequently, in a second circulation U2, the radiation S passes through the filter element 5 and in turn the amplifier medium 3 again. This occurs correspondingly in a third circulation U3 and in possible further circulations.

The radiation thus passes through amplifier medium 3 and filter element 5 alternately. The time which the radiation S requires per circulation corresponds to the optical length $L_U$ of the resonator 19 and is equal to the optical path route between two sequential passages through the filter element 5, divided by the speed of light in vacuum c.

In FIG. 3, as described, a schematic illustration of the light path W according to FIG. 2 is indicated, so that the radiation passes through the same filter element 5 and the same filter medium 3 again and again in chronological sequence. The same signal of a control unit 11, symbolized by a branching double line, is therefore always applied to all filter elements 5 shown, because it is always the same filter element. All filter elements 5 thus have an equal, free and/or passable wavelength range at a specific point in time.

Alternatively, it is also possible that a chain of various filter elements 5 and various amplifier elements 3 is provided in alternating sequence, all filter elements 5 always being passable for the same wavelength range at a specific point in time.

In the exemplary embodiment of a light source described here according to FIG. 4A, the wavelength-tunable light source 1 has an element 23, which is simultaneously used as the output source 2 and as the first amplifier medium 3. The radiation R is generated in operation of the output source 2. This radiation runs, at least partially, in the direction toward an optical circulator 15. The circulator 15 has three terminals A, B, C. Light which enters the circulator 15 through terminal A is output at terminal B. Light which enters terminal B is output at terminal C.

The radiation R of the output source 2 enters the circulator at terminal B and is relayed to terminal C. The radiation R, whose total power $P_A$ is approximately 1 mW, subsequently passes through the first filter element 5. The partial radiation P of the radiation R is transmitted by the first filter element 5. The power of this transmitted partial radiation P is approximately 3 µW. To set the polarization of the partial radiation P, it runs through a polarization controller 8a. The partial radiation P then enters the circulator 15 at terminal A and is relayed to the terminal B. The partial radiation P then passes through the element 23 and/or the first amplifier medium 3, which has a polarization-dependent amplification. The polarization of the partial radiation P is set via the polarization controller 8a so that a maximum amplification of the partial radiation P occurs in the amplifier medium 3.

Optionally, the partial radiation P which is amplified by the first amplifier medium 3 can pass through a further polarization controller 8b. An optical isolator 9, which is also optional, is situated downstream from this second polarization controller 8b, a transmission direction of the isolator 9 being designated by an arrow. The second filter element 6 follows the isolator 9. The filter elements 5, 6 are tuned by the control unit (not shown) so that the runtime difference of the partial radiation P from the first filter element 5 to the second filter element 6 is compensated for, so that a high tuning speed is achievable with respect to the wavelength of the partial radiation P.

Referring to FIG. 4B, the second filter element 6 suppresses the broadband emission emitted by the output source 2, which forms the radiation R and runs in the direction toward the second filter element 6. This radiation R, up to radiation in the spectral range of the partial radiation P, thus does not reach the second amplifier medium 4. The partial radiation P is amplified once again via the second amplifier medium 4 and subsequently leaves the light source 1.

The individual components of the light source 1 are optically connected via optical fibers, which are implemented using glass fibers.

The element 23 is implemented as a fiber-coupled optical semiconductor amplifier, for example. A saturation power $P_{sat}$ of this element 23, i.e., the maximum light power which it can emit, is a few tens of milliwatts. A central wavelength of the radiation R is approximately 1310 nm. The element 23 displays a polarization-dependent amplification, the polarization dependence being approximately 16 dB. A small signal amplification factor G of the element 23 is approximately 25 dB, correspondingly a factor of approximately 300.

First filter element 5 and second filter element 6 are fiber-based, tunable fiber-Fabry-Perot filters, also designated as fiber-Fabry-Perot-tunable filters, abbreviated as FFP-TF. The filter elements 5, 6 have a bandwidth of approximately 0.3 nm. This bandwidth also corresponds to the spectral width of the partial radiation P. A free spectral range of the filter elements 5, 6 is approximately 130 nm. The filter elements 5, 6 may be tuned within the free spectral range. The filter elements 5, 6 each transmit a radiation which has wavelengths of the partial radiation P. Other wavelengths are reflected back in the direction toward the element 23 by the filter elements 5, 6 and absorbed by the circulator 15 and/or by the isolator 9. The filter elements 5, 6 display a suppression of approximately 30 to 40 dB, outside the spectral range of the partial radiation P.

At a spectral width of the transmission window $B_P$ of 0.3 nm, a spectral width of the radiation R emitted by the element 23 of approximately 100 nm, a small signal amplification factor G of 25 dB, and the total power $P_A$ of the radiation R of approximately 1 mW, the product of G, $P_A$, and ($B_P/B_A$) is approximately 0.9 mW. This value is significantly less than the saturation power $P_{sat}$ of the element 23 of approximately 50 mW. In other words, the power of the partial radiation P after passing through the element 23 is significantly less than the saturation power $P_{sat}$. Because the element 23 is not operated in saturation, the spontaneous emission of the element 23 is not suppressed and a simultaneous use as an output source 2, which emits a spectrally broadband radiation R, and as a first amplifier medium 3 is made possible.

FIG. 5 shows the time-averaged spectrum of the light emitted by the light source 1 shown in FIG. 4. That is, time averaging is performed over the spectra of the partial radiation P emitted at various times, so that the entire spectral range emitted by the tunable light source 1 is shown. The intensity I of the partial radiation P in dB is plotted in relation to the wavelength λ in nm. Over a spectral range having a width of approximately 100 nm from approximately 1265 nm to 1365 nm, the spectral intensity I is uniform to approximately 5 dB. The light source 1 thus represents a spectrally broadband light source 1. The central wavelength is approximately 1310 nm. The time-averaged power of the partial radiation P emitted by the light source 1 is approximately 50 mW to 100 mW.

In FIG. 6, the intensity I of the emitted partial radiation P is plotted linearly in relation to the time t. The tuning frequency of the filter elements 5, 6 is approximately 56 kHz, corresponding to a period duration $T_P$ of approximately 18 μs. During one period duration, each wavelength is set multiple times during one period via the bidirectional travel of the fiber-Fabry-Perot filter, one or multiple times upon enlargement of the spacing of the ends of the optical fibers forming the fiber-Fabry-Perot filter, and one or multiple times upon reduction of the spacing. An effective tuning frequency of the partial radiation P is thus approximately 112 kHz, corresponding to twice 56 kHz. Upon enlargement or reduction of the spacing of the filter elements 5, 6, slight intensity variations are noticeable, i.e., only every second maximum of the curve shown in FIG. 6 displays equal intensity.

The curve shown in FIG. 6 has an approximately Gaussian form in the area of the individual maxima. This shape similar to a bell curve is advantageous, for example, for a subsequent Fourier transform of the intensity, for example, in the context of a tomographic application in the field of medicine. In order to achieve a more uniform time curve of the power of the partial radiation P emitted by the light source 1, a driver current of the first amplifier medium 3 and/or second amplifier medium 4 can optionally be set as a function of time. The amplification of the amplifier media 3, 4 thus also changes as a function of time and a time-dependent setting of the power of the partial radiation P is possible.

The intensities I of the driver signals of the control unit 11 for the filter elements 5, 6 and an interferogram of the partial radiation P, each plotted linearly in relation to the time t, are shown in FIG. 7. For example, a frequency generator generates a harmonic signal having a frequency of 56 kHz, see the curve designated by D. This signal is amplified and superimposed with a DC signal. The driver signal, curve E, for the first filter element 5 results therefrom. The driver signal for the second filter element 6, curve F, is similarly generated from the signal of the function generator. The driver signals of first filter element 5 and second filter element 6 have a phase shift to one another, see curves E and F, which approximately corresponds to one-twentieth of the period duration $T_P$.

Furthermore, an interferogram is shown, curve G. This interferogram is recorded at the output of a Mach-Zehnder interferometer having different arm lengths, difference of the arm lengths approximately 1 mm, using a differential detector. The curve G displays significant oscillation. This oscillation of the curve G results from the time curve of the wavelength of the partial radiation P emitted by the light source 1.

FIG. 8 shows a corresponding illustration to FIG. 7. However, the driver frequency is 170 kHz, corresponding to 340,000 wavelength passages per second. The axis in relation to the time t is adapted correspondingly. The wavelength tuning range, over which the partial radiation P is swept, is approximately 50 nm, in comparison to approximately 100 nm according to FIG. 7. The output power of the light emitted by the light source 1, averaged over time, is approximately 30 mW. As a result of the smaller tuning range of 50 nm and the linear curve of the intensity curve I in this narrower wavelength range, compare FIG. 5, the interferogram, see curve G, has a more uniform intensity distribution compared to FIG. 7.

FIG. 9 shows a point spread function, abbreviated PSF, analogous to an application for optical coherence tomography, measured on a simplified structure. The signal amplitude Y or Y' is plotted in arbitrary units, linearly in FIG. 9A and logarithmically in FIG. 9B, in relation to an arm length difference D of an interferometer in mm. The attenuation of the signals is approximately 20 dB up to a value of approximately 3 mm. This means that up to an optical layer thickness of approximately 3 mm, for example, a signal can be obtained by interferometry in the context of an optical coherence tomography application, for example. The arm length difference is also a measure of the mean integrated line width of the partial radiation P. The mean integrated line width corresponds well to the line width of 0.3 nm which is predetermined by the filter elements 5, 6. The light source 1 is thus suitable for tomographic applications, for example.

Exemplary embodiments of wavelength-tunable light sources 1 are shown in FIGS. 10 through 20, in which the radiation R and/or the partial radiation P passes through at least one component at least twice. The control unit is not shown in each case.

Figure 10:
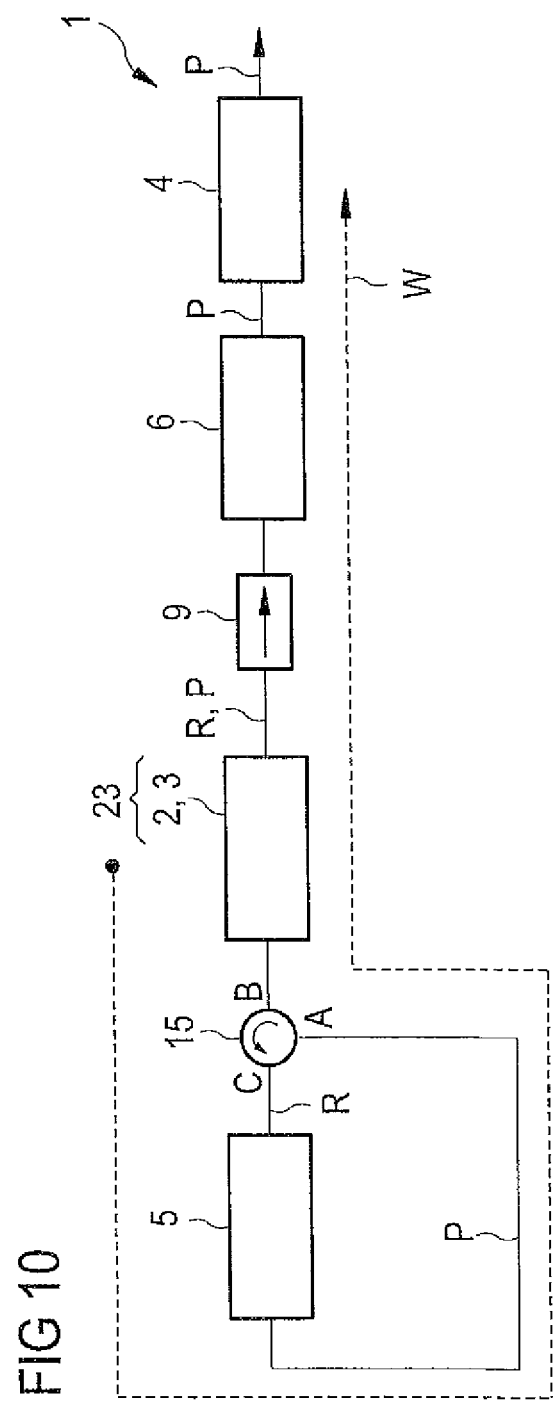

The exemplary embodiment of the light source 1 according to FIG. 10 essentially corresponds to that shown in FIG. 4. Output source 2 and first amplifier medium 3 are formed by the same element 23, which displays polarization-independent amplification. In this way, the polarization controller is dispensed with.

Figure 11:
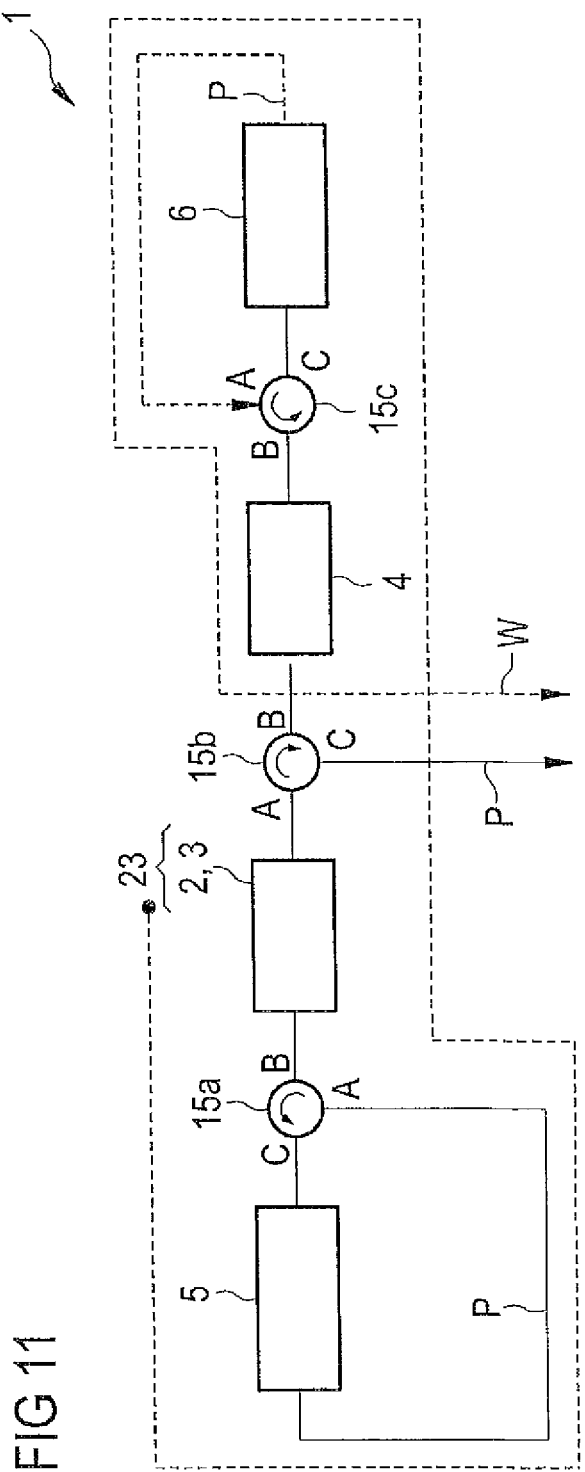

In the exemplary embodiment according to FIG. 11, the light source 1 has three circulators 15a, 15b, 15c. A passage twice through the first amplifier medium 3 and the second amplifier medium 4 is possible via the circulators 15b, 15c. The light path W is illustrated by an arrow-dashed line. A high power of the partial radiation P is ensured by the passage twice through the second amplifier medium 4. This allows the spectral width of the partial radiation P to be reduced, for example.

Figure 12:
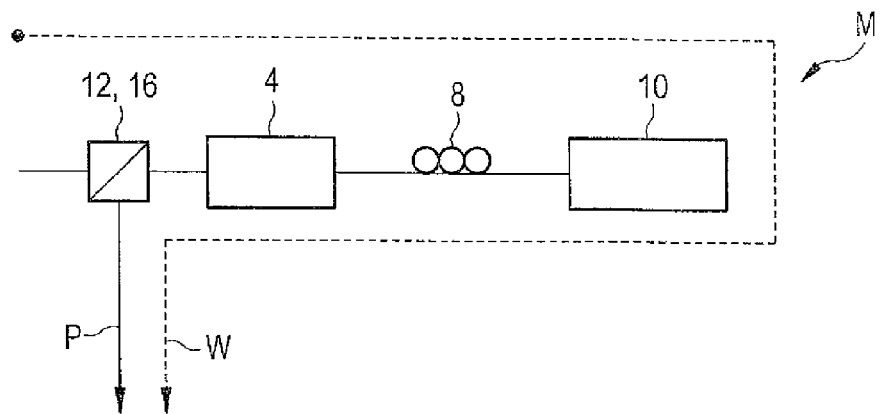

FIG. 12 shows a module M, which can be used instead of the second amplifier medium 4 according to FIG. 4 or FIG. 10, for example. The preferably linearly polarized partial radiation P is transmitted by a polarization-selective component 12, which is designed as a polarization beam splitter 16, and passes through the second amplifier medium 4. The polarization is subsequently rotated via the polarization controller 8. The radiation is reflected by a mirror 10, which can be designed as a metal mirror, dielectric mirror, or as a Faraday mirror, and passes through the polarization controller 8 once again, whereby the polarization is effectively rotated by 90°, for example. The partial radiation subsequently passes through the second amplifier medium 4, which amplifies polarization-independently, again. Because the polarization of the partial radiation is now rotated by 90° as a result of the passage of the polarization controller 8 twice, the amplified partial radiation P is coupled out of the light source 1 by polarization beam splitter 16.

Figure 13:
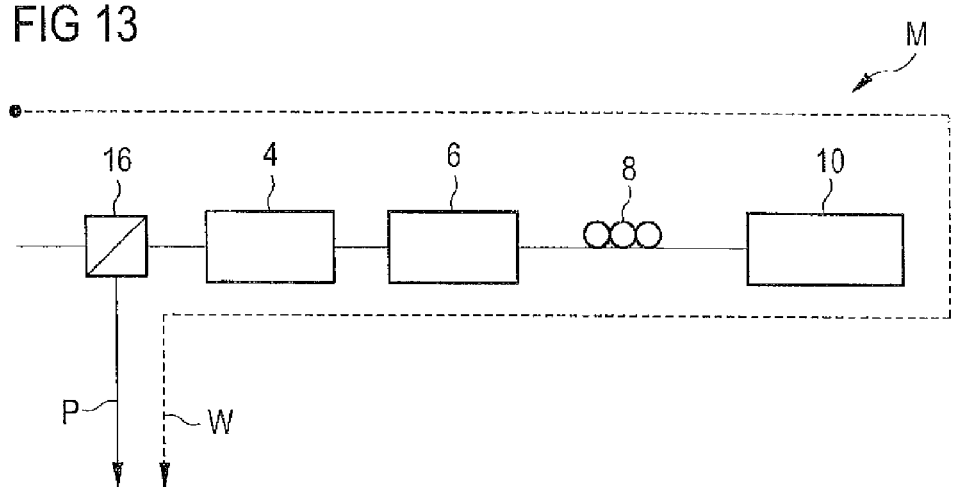

A variant of the module M shown in FIG. 12 is illustrated in FIG. 13. The second filter element 6 is attached between the second amplifier medium 4 and the mirror 10. The partial radiation P thus also passes through the second filter element 6 twice. In this way, a high suppression of the spectrally broadband background of the radiation R of the output source 2 is ensured.

Figure 14:
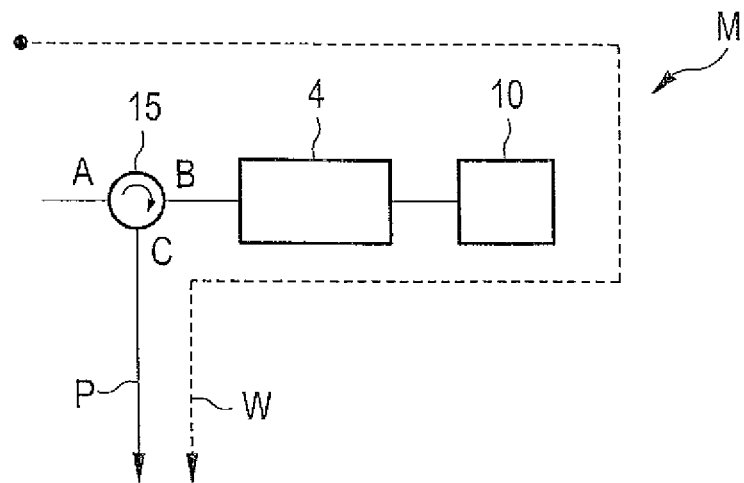
Figure 15:
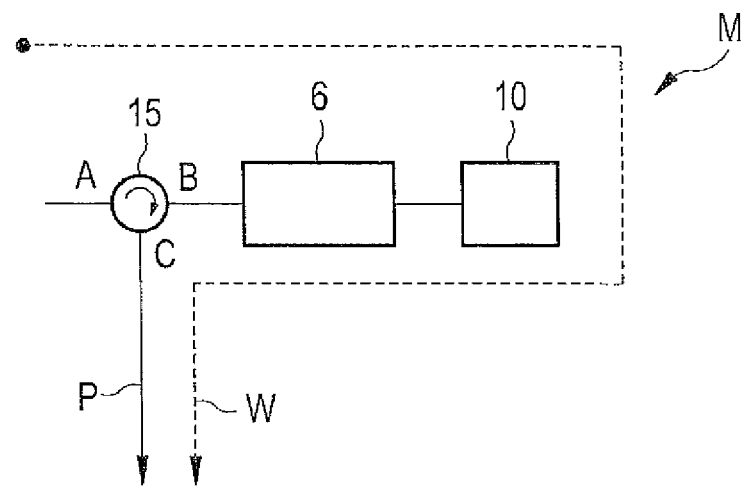

Instead of the polarization-selective element 12 according to FIGS. 12 and 13, a circulator 15 is used in FIGS. 14 and 15. The second amplifier medium 4, see FIG. 14, can be implemented as polarization-selective. Instead of the second amplifier medium 4, which the radiation passes through twice, a second filter element 6 can alternatively or also additionally be used, see FIG. 15. The mirror 10 is preferably not polarization-selective in this configuration. The second filter element 6 has a transmissive-absorptive effect, i.e., non-transmitted light is absorbed and not conducted back via reflection in the direction toward the first amplifier medium (not shown).

Figure 16:
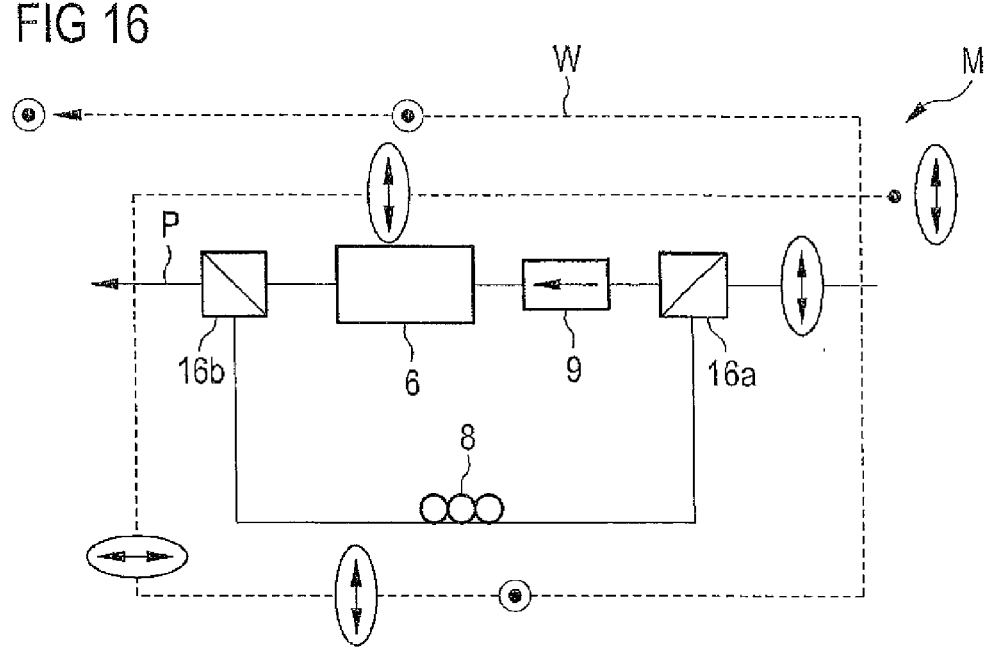

The use of a transmissive-reflective second filter element 6, which the radiation passes through twice, is shown in FIG. 16. The module M shown in FIG. 16 can be used instead of the module M shown in FIG. 15 in a light source 1 according to FIG. 4 or FIG. 10, for example. In the module M according to FIG. 16, light polarized parallel to the plane of the drawing, symbolized by a circled double arrow, is coupled in. If the partial radiation P has light having polarization perpendicular to the plane of the drawing, it is symbolized by a dot in a circle. This passes through the polarization beam splitter 16a and the isolator 9 and reaches the transmissive-reflective second filter element 6. The light which is not transmitted and is reflected by the second filter element 6 is absorbed by the isolator 9. The partial radiation P is reflected via the polarization beam splitter 16b, passes through the polarization controller 8, which is implemented as a Faraday rotator, for example, is reflected by the polarization beam splitter 16a, passes through the second filter element 8 a further time, and is coupled out via the polarization beam splitter 16b.

Figure 17:
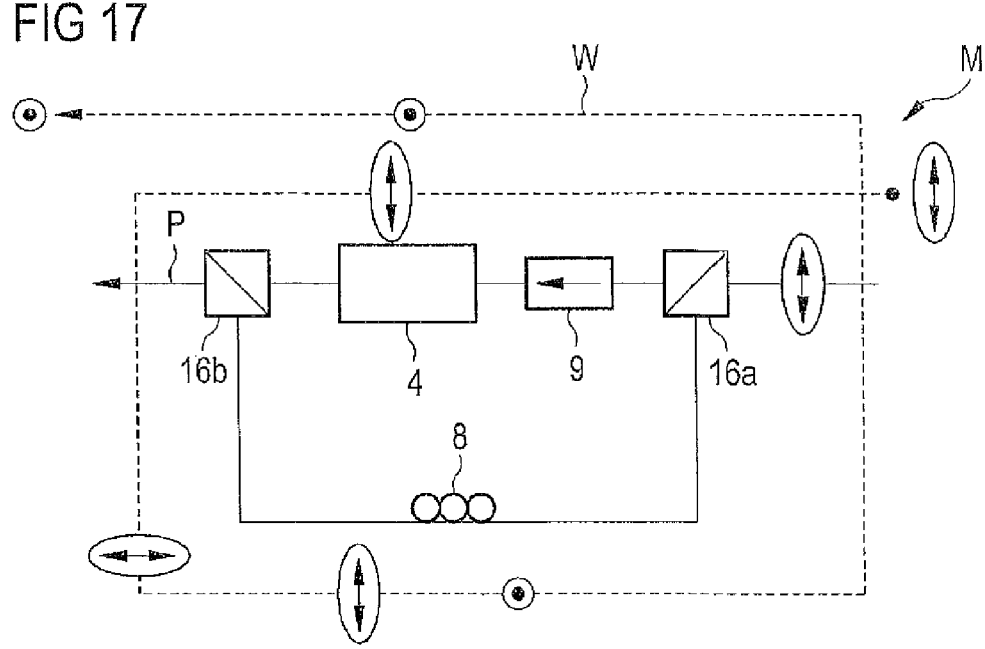

A corresponding module M is shown in FIG. 17, alternatively or additionally to the second filter element 6, a second amplifier medium 4 also being used. The optical isolator 9 is optional and is used to suppress the spectrally broadband background, which can be emitted by the second amplifier medium 4.

The fourfold usage of a transmissive-absorptive second filter element 6 is illustrated in FIG. 18. A compound module MM has a module M. The module M can correspond to the configuration shown in FIG. 16, for example, the optical isolator 9 provided according to FIG. 16 being dispensed with. The second filter element 6 is additionally preferably designed according to FIG. 18 as a transmissive-absorptive filter element.

Alternatively or additionally, the fourfold usage of a polarization-independent amplifier medium 4 is schematically shown in FIG. 18. The module M is then designed according to FIG. 17, for example, the optical isolator 9 shown in FIG. 17 being dispensed with.

According to FIG. 19, the compound module MM has both a module Ma according to FIG. 16 and also a module Mb according to FIG. 17, the second amplifier medium 4 being a polarization-independent amplifier medium and the second filter element 6 being a transmissive-absorptive filter. The optical isolators 9 shown in FIGS. 16 and 17 are each left out. A polarization controller can optionally be attached between the modules.

The exemplary embodiments of a light source 1 shown in FIGS. 10 through 19 do not represent an exhaustive list, rather multiple modules M and/or compound modules MM may also be nested and combined, in order to achieve longer chains of amplifier media 3, 4 or filter elements 6, for example, which the radiation passes through multiple times. Depending on the concrete demands on the light source 1, additional amplifier media 3, 4 or filter elements 5, 6 may also be integrated in the light source 1, as well as additional components such as shutters, polarization controllers 8, or polarizers 16.

A configuration for generating a regulating signal for activating the filter elements 5, 6 is illustrated in FIG. 20. For example, the amplifier media 3, 4 are not shown for simplification of the illustration. FIG. 21 shows the activation of two filter elements 5, 6, further second filter elements 6 may also be activated similarly.

After the first filter element 5, a small part of the partial radiation P is coupled out, for example, via a fiber coupler. The coupled-out partial radiation P is conducted according to FIG. 20 to three separate detectors 13a, which are implemented as photodiodes, for example. A wavelength-selective element 14 is located in front of each detector 13a. The wavelength-selective elements 14 are implemented as band-pass filters, for example, which may comprise a fiber-Bragg grating in combination with a circulator or a coupling configuration. It is also possible that the wavelength-selective elements 14 are only implemented as band-stop filters made of a fiber-Bragg grating in transmission, also in combination with an AC voltage-coupled detector 13a. Edge filters, based on colored glass, may also be used, for example.

In case of a predetermined, chronologically periodic tuning of the wavelength of the partial radiation P, amplitude, zero point shift, and phase in relation to the wavelength time curve of the partial radiation P transmitted by the first filter element 5 may be ascertained via the detectors 13a. A time shift because of temperature changes or variations of the response function of the first filter element 5 may be compensated for.

For synchronization of the second filter element 6 to the first filter element 5, a part of the radiation reflected by the second filter element 6 is deflected to a detector 13b. Alternatively or additionally, a part of the light transmitted by the second filter element 6 is conducted to a detector 13c downstream from the second filter element 6. In contrast to the illustration in FIG. 20, wavelength-selective elements 14 may optionally also be located in front of the detectors 13b, 13c.

The time curve of the wavelength $\lambda$ is plotted in relation to the time t in FIG. 21, see uppermost curve in FIG. 21. If the partial radiation P has a specific wavelength, one of the detectors 13a receives a signal having an intensity I, see the three lowermost curves in FIG. 21. The wavelengths at which a signal is received may be set via the wavelength-selective elements 14. The signals of the detectors 13a may be used for automatic regulation via the control unit. Thus, for example, the spectral range over which the partial radiation P is tuned, and/or the intensity of the partial radiation P are automatically regulated. Further parameters which may be regulated are driver voltage, zero point shift, or phase shift of the driver signals.

The signals of the detectors 13b, 13c are shown as a function of the time t in FIG. 22 for the case in which first filter element 5 and second filter element 6 are not adapted to one another in regard to the time delay T. In this case, a different wavelength of the partial radiation P transmitted by the first element 5 is applied to the second filter element 6, curve K in FIG. 22, than the wavelength which is transmitted by the second filter element 6 at this moment, see curve J in FIG. 22. i.e., the wavelength applied to the second filter element 6 is spectrally shifted in relation to the wavelength transmitted by the second filter element 6. Because of the periodic curve of the wavelengths, the two curves J, K only intersect at two points per period. These intersection points are shown by thin vertical lines.

If the two curves J, K intersect, this means that the partial radiation applied to the second filter element 6 is transmitted by the second filter element 6. In other words, at this point in time less or no partial radiation is reflected by the second filter element 6 back in the direction of the first filter element 5. Therefore, the signal intensity drops at the detector 13b. The detector 13c displays a signal when radiation is transmitted by the second filter element 6.

If both curves J, K lie one above another, the detector 13b does not display a signal at any point in time, while the detector 13c always displays a signal. First filter element 5 and second filter element 6 are thus automatically adaptable to one another via a control loop, in that, for example, the signal of the detector 13b is minimized and/or the signal of the detector 13c is maximized.

In the exemplary embodiments according to FIGS. 4 and 10 through 22, fiber-Fabry-Perot filters are used in each case as the filter elements 5, 6, which have a transmissive-absorptive or transmissive-reflective action.

In the exemplary embodiment according to FIG. 23, a further possible implementation of the filter elements 5, 6 is illustrated. The radiation R, which originates from the output source 2, for example, which is not shown in FIG. 23, is deflected onto an optical diffraction grating, which forms the first filter element 5. Various wavelength components of the radiation R are reflected in various directions by the diffraction grating, see thin arrows in FIG. 23. The reflected radiation R reaches a polygonal mirror rotating around a rotational axis 18 at an angular velocity 20, which forms the second filter element 6. The chronologically variable position of the polygonal mirror is symbolized by a dashed line. The radiation R is not incident perpendicularly on a surface of the polygonal mirror. The radiation R is reflected by the polygonal mirror to the mirror 10, which reflects the radiation R back to the polygonal mirror. The radiation R is reflected back to the first filter element 5 by the polygonal mirror.

The light reflected back from the first filter element 5 in the direction of the output source (not shown) now only runs parallel to the incident radiation R if the second filter element 6 and/or the polygonal mirror are each located in the correct position during the incidence of the radiation R twice on the polygonal mirror. Otherwise, the radiation R or the partial radiation P cannot pass through the filter elements 5, 6 without being filtered out. Filtering of the radiation R thus occurs through the interplay of spectrally splitting first element 5 and second filter element 6, which reflects at different angles as a function of time, so that at specific times only a partial radiation P of a specific wavelength can pass through the configuration. The tuning speed of the filter elements 5, 6 and the time curve of the wavelength of the partial radiation P are a function of the angular velocity 20.

Optionally, multiple facets of the polygonal mirror may be used simultaneously for filtering multiple beams, i.e., modules M may be formed. Because the various facets of the polygonal mirror have a fixed, chronologically constant phase relationship to one another, the synchronization of the two filter events, each upon incidence on the various facets of the polygonal mirror, is simplified. It is also possible that the radiation passes through amplifier media 3, 4, which may be placed so that only partial radiation P reflected at the correct angle by the polygonal mirror is amplified.

Because the angular velocity of the polygonal mirror is settable very precisely and can also be kept constant with high precision, and by the fixed selection of a reflection angle on the mirror 10, a synchronous tuning of the filter elements to one another upon incidence on the first filter element 5 implemented as gratings as the radiation R or the partial radiation P passes forward or backward is achievable in a simple way.

The polygonal mirror 21 has a diameter of 3 to 4 cm and approximately 20 facets, for example. In contrast to the other exemplary embodiments, the radiation R or the partial radiation P is not conducted in an optical fiber in the filter configuration according to FIG. 23. In order to make separation of the incoming radiation R of the configuration from the outgoing partial radiation easier, for example, they may be offset perpendicularly to one another with respect to the plane of the drawing.

A further module M for an exemplary embodiment of the light source is schematically illustrated in FIG. 24. The module M has two delay routes 24, which are connected optically in parallel to bypass routes 25 via fiber couplers 26. Both the delay routes 24 and also the bypass routes 25 are implemented by optical fibers 7. The delay routes 24 and the bypass routes 25 are preferably situated downstream from a last of the filter elements of the light source (not shown in FIG. 24).

The radiation is split into the delay routes 24 and into the bypass routes 25 by the fiber couplers 26 or also by beam splitters. The delay routes 24 according to FIGS. 24 and 25 have a length between 100 m and 5 km inclusive for this purpose, for example, while in contrast the bypass routes 25 have a significantly shorter optical path length, for example, less than 50 m, in particular less than 1 m. The two delay routes 24 may have identical optical lengths or also optical lengths which are different from one another. In particular, one of the delay routes 24 can have twice as great an optical length as the second delay route.

In other words, the radiation P is split into at least two parts, the part of the radiation P which passes through one of the delay routes 24 or through both delay routes 25 reaching an output 27a, 27b of the module M or the light source later because of the greater optical path length than the part of the radiation P which passes through the bypass routes 25. The same wave train is thus divided in regard to the intensity into the delay routes 24 and the bypass routes 25 and is emitted with a time delay at the outputs 27a, 27b of the module M or the light source. A tuning rate or a repetition rate of wave trains of the light source can thus be increased using such a module M.

The module M according to FIG. 24 has precisely two delay routes 24. A tuning rate of the light source having such a module M according to FIG. 24 can thus be multiplied by four. Notwithstanding the illustration according to FIG. 24, the module M can also only have one delay route 24 or more than two delay routes 24. It is possible that the two outputs 27a, 27b may be merged into one single output, notwithstanding the illustration of FIG. 24. Preferably, a second amplifier medium, which is not shown in FIG. 24, is situated downstream from at least one of the outputs 27a, 27b or a merged output.

In the module M according to FIG. 25, the delay route 24, which is connected optically in parallel to the bypass route 24, is located between the first filter element 5 and two second filter elements 6a, 6b. A part of the radiation P thus passes through the delay route 24, a different part of the radiation P passes through the bypass route 25, which has a shorter optical length than the delay route 24. The two parts of the radiation P may be conducted to the two second filter elements 6a, 6b and to the outputs 27a, 27b by the fiber coupler 26, which follows the delay route 24 and the bypass route 25.

A first amplifier medium and/or a second amplifier medium (not shown in FIG. 25) are preferably situated between the first filter element 5 and at least one of the second filter elements 6a, 6b. In contrast to the illustration in FIG. 25, the outputs 27a, 27b may be merged. Furthermore, it is possible that one light source has a plurality of the modules M.

The invention described here is not restricted by the description on the basis of exemplary embodiments. Rather, the invention comprises every novel feature and every combination of features, which particularly includes every combination of features in the claims, even if this feature or this combination itself is not explicitly disclosed in the claims or exemplary embodiments.

This patent application claims the priority of German Patent Application 10 2008 045 634.9, the content of whose disclosure is hereby incorporated by reference.

The invention claimed is:

1. A method of selectively transmitting electromagnetic radiation from an output source comprising the steps of:
generating electromagnetic radiation (R) having a wavelength range from the source;
tuning a first filtering element to obtain a partial wavelength range (P) of the wavelength range;
amplifying the partial wavelength range (P) of the wavelength range of the output source; and
tuning a second filtering element to obtain an amplified filtered partial wavelength range,
wherein the tuning of the first filtering element and the tuning of the second filtering element is delayed by a time T to permit the transmission of the amplified filtered partial wavelength range, wherein a tuning frequency of at least one of the first filtering element or the second filtering element is at least temporarily at least 40 kHz.

2. The method of claim 1 further comprising the step of tuning the first filter such that the partial radiation range P varies over a range of wavelengths.

3. The method of claim 1 further comprising the step of performing a tomography scan using the amplified partial wavelength range.

4. The method of claim 1 wherein a filtering effect of the first filter element or the second filter element is based on one or more of absorption, reflection, transmission, refraction, or diffraction.

5. The method of claim 1 further comprising the step of synchronizing the first filter and the second filter such that each filter transmits over a spectra of the partial wavelength range P.

6. The method of claim 1 wherein the steps of generating electromagnetic radiation (R) having a wavelength range from the source and amplifying the partial wavelength range (P) of the wavelength range of the output source are performed by the same optical element.

7. The method of claim 1 wherein the step of amplifying is performed using a resonatorless amplifier.

8. A method of selectively transmitting electromagnetic radiation from an output source comprising the steps of:
generating electromagnetic radiation (R) having a wavelength range from the source;
filtering the electromagnetic radiation (R) to obtain a partial wavelength range (P) of the wavelength range;
amplifying the partial wavelength range (P) of the wavelength range of the output source; and
filtering the partial wavelength range (P) to obtain an amplified filtered partial wavelength range,
wherein filtering the electromagnetic radiation (R) and filtering the partial wavelength range (P) is delayed by a time T to permit the transmission of the amplified filtered partial wavelength range, wherein a tuning frequency of a first filter element during filtering is at least temporarily at least 40 kHz.

9. The method of claim 8 wherein filtering of the electromagnetic radiation (R) and filtering of the partial wavelength range (P) is performed with the first filter element.

10. The method of claim 9 further comprising the step of guiding the partial wavelength range (P) to the first filter element.

* * * * *

UNITED STATES PATENT AND TRADEMARK OFFICE
CERTIFICATE OF CORRECTION

PATENT NO. : 8,810,901 B2
APPLICATION NO. : 13/061090
DATED : August 19, 2014
INVENTOR(S) : Robert Alexander Huber et al.

It is certified that error appears in the above-identified patent and that said Letters Patent is hereby corrected as shown below:

On the title page of the patent, Item (73), the assignee name should read "Ludwig-Maximilians-Universität München" and not Lightlab Imaging, Inc.

Signed and Sealed this
Eighteenth Day of November, 2014

Michelle K. Lee
*Deputy Director of the United States Patent and Trademark Office*